United States Patent [19]
Anderson et al.

[11] Patent Number: 5,736,347
[45] Date of Patent: Apr. 7, 1998

[54] **NUCLEIC ACIDS OF *ROCHALIMAEA HENSELAE* AND METHODS AND COMPOSITIONS FOR DIAGNOSING *ROCHALIMAEA HENSELAE* AND *ROCHALIMAEA QUINTANA* INFECTION**

[75] Inventors: Burt E. Anderson, Valrico, Fla.; Russell L. Regnery, Tucker, Ga.

[73] Assignee: The United States of America as represented by the Department of Health and Human Resources, Washington, D.C.

[21] Appl. No.: 307,279

[22] Filed: Sep. 16, 1994

Related U.S. Application Data

[63] Continuation-in-part of Ser. No. 245,294, May 18, 1994, Pat. No. 5,644,047, which is a continuation-in-part of Ser. No. 822,539, Jan. 17, 1992, Pat. No. 5,399,485.

[51] Int. Cl.$^6$ .................. G01N 33/554; C12Q 1/68; C07K 16/00
[52] U.S. Cl. .................. 435/7.32; 435/6; 435/975; 436/811; 530/388.4; 530/387.1; 530/389.5; 530/391.1; 530/391.3
[58] Field of Search .................. 435/7.32, 6, 975; 436/811; 530/388.4, 387.1, 389.5, 391.1, 391.3

[56] References Cited

U.S. PATENT DOCUMENTS 5,399,485  3/1995  Regenery et al. .................. 435/7.32

OTHER PUBLICATIONS

Anderson et al., *J. Clin. Micro.* 32(4):942–948, 1994.
Roop et al, *Infect. Immun.*, 62(3):1000–1007, 1994.
Anderson et al. "Molecular Cloning . . . " Abstract D–90, 93rd Gen. Meeting Amer. Soc. for Microbiol., Atlanta, GA 1993.
Koehler et al, *N. Eng. J. Med.* 327(23):1625–1631, 1992.
Anderson et al. *Amer. Soc. for Rickettsiology and Rickettsial Dis.* p. 16, Apr. 13, 1991.
Regnery et al. *Amer. Soc. for Rickettsiology and Rickettsial Dis.* p. 37, Apr. 13, 1991.
Brenner et al. *J. Clin. Micro.* 29:1299–1302, 1991.
O'Connor et al. *J. Clin. Micro.* 29:2144–2150, 1991.
Brenner et al. *J. Clin. Micro.* 29:2450–2460, 1991.
Cockerelle et al. *N. Eng. J. Med.* 324:1511–1512, 1991.
Birtles et al. *N. Eng. J. Med.* 325:1447–1448, 1991.
Relman et al. *N., Eng. J. Med.* 323:1573–1580, 1990.
Slater et al. *N. Eng. J. Med.* 323:1587–1593, 1990.
Schlossberg et al. *Arch. Intern. Med.* 149:1437–1439, 1989.
English et al. *JAMA.* 259:1347–1352, 1988.
Angritt et al. *Lancet* 1:996, 1988.

*Primary Examiner*—James C. Housel
*Assistant Examiner*—Jennifer Shaver
*Attorney, Agent, or Firm*—Fitch, Even, Tabin & Flannery

[57] ABSTRACT

A method of diagnosing cat scratch disease and a method of diagnosing bacillary angiomatosis in a subject by detecting the presence of *Rochalimaea henselae* or an antigenic fragment thereof in the subject is provided. Also provided is a vaccine comprising an immunogenic amount of a nonpathogenic *Rochalimaea henselae* or an immunogenically specific determinant thereof and a pharmaceutically acceptable carrier. A method of diagnosing *Rochalimaea quintana* infection in a subject by detecting the presence of a nucleic acid specific to *Rochalimaea quintana* in a sample from the subject is provided. A purified, 60-kDa heat shock protein of Rochalimaea is provided. Also provided is a 17-kDa antigenic polypeptide of Rochalimaea.

7 Claims, 2 Drawing Sheets

| | | | | |
|---|---|---|---|---|
| ROCHALIMAEA HENSELAE | (19) | 10/34 | 16/32 | 8/32 |
| ROCHALIMAEA VINSONII | 10.8 | (15) | 8/28 | 6/28 |
| ROCHALIMAEA QUINTANA | 6.0 | 11.0 | (13) | 8/26 |
| RICKETTSIA PROWAZEKII | 12.2 | 13.6 | 10.3 | (13) |

DISTRIBUTION OF ANTIBODY TITERS AMONG PERSONS DIAGNOSED WITH CAT SCRATCH DISEASE SYNDROME

N = 40
MINIMUM POSITIVE TITER = 1/64

DISTRIBUTION OF ANTIBODY TITERS AMONG HEALTHY PERSONS

N = 107
MINIMUM POSITIVE TITER = 1/64

| SPECIES | CAT1 | RH1/RQ1 | CAT2 (C) |
|---|---|---|---|
| R. HENSELAE | GATTCAATTGGTTTGAAGGAGGCT (SEQ ID NO:1) | GGTGCGTTAATTACCGATCC (SEQ ID NO:5) | GAATACGTCCTGGTGATGTGA (SEQ ID NO:3 COMPLEMENT) |
| R. QUINTANA | ................A...... (SEQ ID NO:2) | ..C..T..G.....T..... (SEQ ID NO:6) | ........C............ (SEQ ID NO:4 COMPLEMENT) |
| R. ELIZABETHAE | .....G...A......C.A..A..A | .....T.NGG.G..T..... | ND |
| R. VINSONII | ..C.....A........A....AC | .....T.....C..T..... | ND |

5,736,347

1

NUCLEIC ACIDS OF ROCHALIMAEA HENSELAE AND METHODS AND COMPOSITIONS FOR DIAGNOSING ROCHALIMAEA HENSELAE AND ROCHALIMAEA QUINTANA INFECTION

This is a continuation-in-part application of application Ser. No. 08/245,294, filed May 18, 1994, now U.S. Pat. No. 5,644,047, which is a continuation-in-part application of application Ser. No. 07/822,539, filed Jan. 17, 1992, now U.S. Pat. No. 5,399,485.

BACKGROUND OF THE INVENTION

Cat scratch disease (CSD) has been the subject of considerable clinical and microbiologic interest for many years. An estimated 7,000 cases of cat scratch disease occur each year in the United States. Due to difficulty in diagnosing CSD and its potentially confusing clinical similarity with other disease syndromes, the number of actual cases of CSD in the United States may be closer to 70,000 per year. CSD is described as a subacute regional lymphadenitis temporally associated with the scratch or bite of a cat, and it occasionally results in meningoencephalitis.

Diagnosis of CSD has been a problem because the etiologic agent of the disease has not been previously identified. An unidentified bacillus has been visualized in biopsies from patients with CSD using Warthin-Starry stain but has resisted identification because of difficulties in obtaining an isolated culture. The etiologic agent of CSD has recently been proposed to be "*Afipia felis*" (7). Despite these efforts, it has not been possible thus far to isolate or otherwise associate this agent with most persons suffering from cat scratch disease.

A clinically related disease, bacillary angiomatosis (BA), is a condition characterized by multiple tumors or swelling due to proliferation of the blood vessels. BA is often found in association with an immunocompromised condition, particularly HIV infection. An unidentified bacillus has been visualized in the angiomatous tissues using Warthin-Starry stain (28). DNA extracted from the angiomatous tissues was shown to contain a fragment of 16S rRNA gene related to, but not identical to, the 16S rRNA gene of *Rochalimaea quintana*. This DNA was not obtained from a pure culture of the organism (28). These investigators were unable to isolate an infectious organism from patient tissues and, therefore, were unable to clearly associate the DNA sequences observed in tissues with an identifiable disease-causing organism. Neither the organism seen in these tissues nor the actual causative agent of the disease was identifiable.

Thus, despite intensive research and widespread effects of the diseases, the etiologic agent(s) of both CSD and BA have evaded identification. This invention describes the identification of an organism, named *R. henselae* herein, which is causative of both diseases.

*R. quintana* has been associated with varied clinical syndromes including persistent fever with bacteremia in normal and immunosuppressed individuals (18, 23, 30, 34). Despite the association of *R. quintana* with disease, *R. quintana*, has not been firmly linked to CSD. Given the controversy surrounding the etiology of CSD and the association *R. quintana* with human disease, there exists a need for a method of directly detecting each of these organisms in lymph node tissue from CSD patients.

The invention meets this need by providing a nucleic acid based method of detecting *R. quintana* infection in a subject. The isolated nucleic acid sequences of the present invention allow primers and probes to be readily designed for such a nucleic acid based detection system.

A need also exists to rapidly identify the presence of infection of a patient by *R. henselae*. Rapid and efficient determination of such infections will aid in the diagnosis of the previously ambiguous symptoms associated with infection by *R. henselae* and therefore facilitate the evaluation of a proper course of treatment.

The present invention meets this need by providing purified antigenic polypeptides necessary for detecting the presence of *R. henselae* antibodies circulating in the serum of patients presently, or previously infected with *R. henselae*. These same purified antigenic polypeptides can be used to produce antibodies which themselves may be utilized in a method to detect the presence of *R. henselae* antigen present in a subject, and therefore determine whether a subject is currently, or has previously been infected with *R. henselae*.

SUMMARY OF THE INVENTION

The present invention relates to a method of diagnosing cat scratch disease and a method of diagnosing bacillary angiomatosis in a subject by detecting the presence of *Rochalimaea henselae* or an immunogenically specific determinant thereof in the subject. Also provided by the present invention is a method of diagnosing cat scratch disease and a method of diagnosing bacillary angiomatosis in a subject by detecting the presence of antibodies in a subject which bind to antigenic determinants of *R. henselae*.

The present invention also provides isolated nucleic acids encoding immunogenic polypeptides of *R. henselae*.

Vectors are also provided comprising the nucleic acids of the present invention. The vectors can be used in a host expression system to produce antigenic polypeptides reagents for diagnostic and prophylactic applications.

The present invention further relates to a method of diagnosing *Rochalimaea quintana* infection in a subject by detecting the presence of a nucleic acid specific to *Rochalimaea quintana* in a sample from the subject.

DETAILED DESCRIPTION OF THE INVENTION

Purified *R. henselae* Antigen

Figures 1, 2:
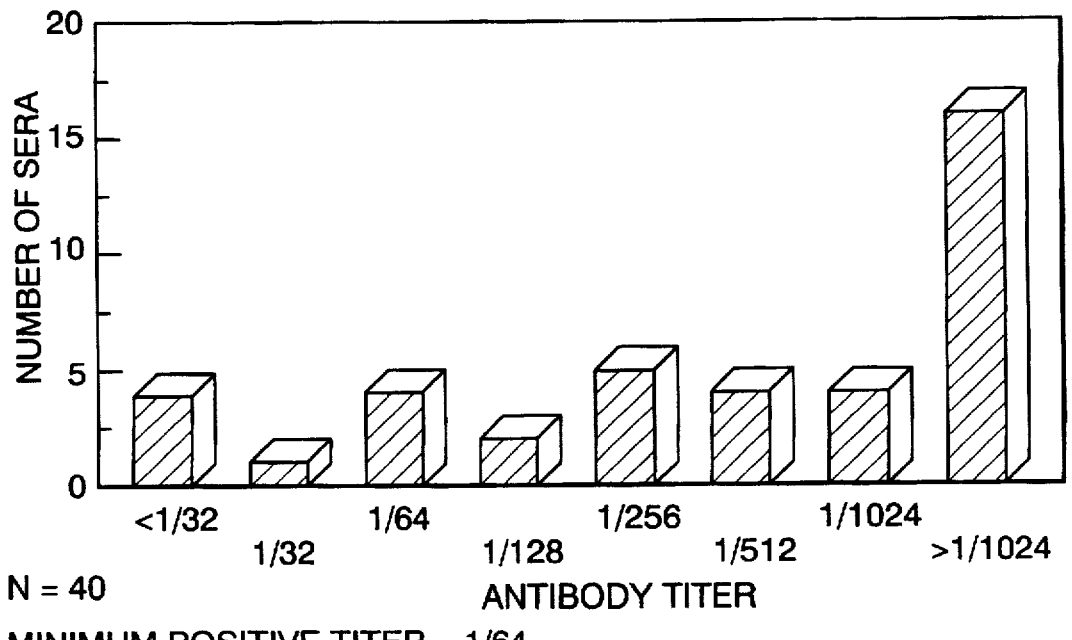
FIG. 1 shows the number of comigrating DNA fragments and the estimated percentage of sequence divergence among organisms related to *R. henselae*. Numbers in parentheses (along the diagonal) indicate the total number of fragments used in analysis of each species. Fractions in the upper right sector indicate the number of comigrating DNA fragments for each pair of species divided by the number of fragments present for both species. Numbers in the lower left sector correspond to the estimated percentage of sequence divergences.
FIG. 2 shows the distribution of *R. henselae* specific antibody titers among persons diagnosed with cat scratch disease syndrome.

The invention provides immunogenically specific proteins or antigenic polypeptide fragments of *R. henselae*. These immunogenically specific proteins or polypeptides are those that specifically bind antibodies that specifically bind *R. henselae*. The immunogenically specific proteins or polypeptide fragments of *R. quintana* are those that specifically bind antibodies that specifically bind *R. quintana*. Specific binding denotes the absence of cross reactivity with antibodies or antigens from organisms other than the specified species. As contemplated herein, an antigen or antibody that is specific for both *R. henselae* and *R. quintana* can bind antibodies or antigens from both of these bacteria, but not antibodies or antigens from other organisms.

An immunogenically specific determinant of *R. henselae* or *R. quintana* can be isolated from the whole organism by chemical or mechanical disruption of the organism. For example, a carbohydrate moiety of the organism can be obtained by standard methods such as digesting the organism with a protease to remove protein moieties.

Alternatively, a protein moiety of *R. henselae* or *R. quintana* can be obtained by treating the whole organism with an ionic detergent such as sodium dodecyl sulfate or a nonionic detergent such as Triton X-100 ($C_{34}H_6O_{11}$ average) or ethylphenyl-polyethylene glycol (NP-40, Shell Oil Company). The protein fragments so obtained can be tested for immunogenicity and specificity as described above. Other immunogenically specific determinants of the organism can be obtained by the standard methods described above.

Immunogenically specific determinants or antigenic polypeptides of this invention can be obtained by synthesizing a vector comprising a nucleic acid sequence encoding an immunogenically specific determinant of *R. henselae* or *R. quintana*. Examples of nucleic acids that encode immunogenic determinants of and *R. henselae* are provided herein, specifically in Examples 3 and 4. The vector can then be placed in a host wherein the immunogenically specific determinant can be synthesized. The selection of a nucleic acid sequence that encodes an immunogenically specific determinant can be accomplished by screening clone libraries of the organism's DNA. Briefly, the bacteria are lysed and the DNA extracted via standard procedure using 1% sodium dodecyl sulfate and proteinase K. The resulting DNA is then partially digested with restriction endonuclease EcoRI, size fractionated and gel purified (agarose gel electrophoresis), and cloned into lambda phage vector lambda ZapII following standard procedures such as described in Maniatis et al. (20). The recombinant plaques are screened for antigen production via ELISA with primary antibody being human or other non-human (e.g., feline) convalescent sera absorbed with an *E. coli* lysate. Alternatively, antigen produced by the recombinant clones can be screened by expressing the antigen and incubating the antigen with antibody-containing serum obtained from patients diagnosed with cat scratch disease. Those recombinant clones expressing *R. henselae*-specific antigen can then be identified by conventional methods (14). Antigen expressing clones are subsequently subcloned and sequenced. Probes can then be derived that are specific for each species.

The subclones expressing species-specific antigens are sequenced and corresponding synthetic peptides can be constructed from the deduced amino acid sequence for use as diagnostic antigens or immunogens. Alternatively, recombinant antigens synthesized from polypeptide-expressing vectors in an appropriate host cell line could be purified by affinity chromatography, polyacrylamide gel electrophoresis, fast peptide liquid chromatography (FPLC), high pressure liquid chromatography, and the like.

For example, the present invention provides an isolated nucleic acid as set forth in the Sequence Listing as SEQ ID NO:11 which encodes a polypeptide with an open reading frame of 148 amino acids with an approximate molecular weight of 17-kDa (17-kilodaltons). As shown in Example 4, this purified polypeptide specifically binds to antibody present in the serum of patients diagnosed with cat scratch disease. This isolated polypeptide, therefore, provides a valuable reagent for diagnostic applications.

Similarly, the present invention also provides an isolated nucleic acid as set forth in the Sequence Listing as SEQ ID NO:7. The polypeptide encoded by this isolated nucleic acid has an open reading frame of 503 amino acids with an approximate molecular weight of 60-kDa (60-kilodaltons) and represents a heat-shock protein encoded by the htrA gene of *R. henselae*. As shown in Example 3, this isolated nucleic acid provides a diagnostic reagent which is valuable in nucleic acid-based detection assays of *R. henselae* infection.

Once the amino acid sequence of the antigen is provided, it is also possible to synthesize, using standard peptide synthesis techniques, peptide fragments homologous to immunoreactive regions of the antigen and test these fragments for their antigenicity using conventional techniques (14). These antigenic fragments can also be modified by inclusion, deletion, or modification of particular amino acid residues in the derived sequences. Thus, synthesis or purification of an extremely large number of peptides derived from the antigens provided is possible.

Similarly, fragments of the antigenic polypeptides provided can be cloned into peptide expression vectors for peptide synthesis in vivo. Such in vivo synthesized polypeptides can be readily purified using techniques such as affinity chromatography.

The amino acid sequences of the present polypeptides can contain an immunoreactive portion of the antigen attached to sequences designed to provide for some additional property, such as solubility. The amino acid sequences of the polypeptides can also include sequences in which one or more amino acids have been substituted with another amino acid to provide for some additional property, such as to remove/add amino acids capable of disulfide bonding, to increase its bio-longevity, alter enzymatic activity, or alter interactions with gastric acidity. In any case, the peptide must possess a bioactive property, such as immunoreactivity, immunogenicity, etc.

A nonpathogenic *R. henselae* or *R. quintana* antigen can be derived by modifying the organism using standard techniques. For example, the whole cell antigen can be subjected to gamma irradiation to render the organism nonpathogenic. Other standard methods of inactivating whole cell antigen include treatment with β-propiolactone or formalin (14).

Determining Antigenicity and Specificity

The antigenicity and specificity of the immunogenic fragments (antigenic polypeptides) or modified whole bacteria can be determined by the usual methods. Briefly, various concentrations of a putative inactivated (nonpathogenic) immunogenically specific determinant are prepared and administered to an animal and the immunological response (i.e., the production of antibodies) of an animal to each concentration is determined. The amounts of antigen or inactivated or modified-live organism administered depends on the subject, e.g. a human or a cat, the condition of the subject, the size of the subject, etc. Thereafter an animal so inoculated to the nonpathogenic antigen can be exposed to the pathogenic organism to test the potential vaccine effect of the immunogenically specific determinant. The specificity of a putative immunogenically specific determinant can be ascertained by testing sera or other fluid from the inoculated animal for cross reactivity with another species (14).

Serological Diagnosis

The present invention provides a method of diagnosing cat scratch disease in a subject comprising detecting the presence of *Rochalimaea henselae* or an immunogenically specific determinant thereof (hereinafter collectively referred to as "*R. henselae* antigen") in the subject. The subject can be a human or other animal. As used herein, an "immunogenically specific determinant" can be on an intact *R. henselae* or an antigenic fragment of *R. henselae*.

Given the subject discovery that the presence of *R. henselae* is associated with cat scratch disease, bacillary angiomatosis and splenic hepatic peliosis, many well-known methods of detecting a bacteria can be applied to detect *R. henselae* and diagnose a disease. In one example of the method of diagnosing cat scratch disease, the step of detecting *R. henselae* antigen is performed by contacting a fluid or tissue sample from the subject with an amount of a purified ligand, e.g. antibodies or antibody fragments, that specifically bind *R. henselae* antigen and detecting the reaction of the ligand with *R. henselae* antigen. As contemplated herein, the term "antibody" includes an intact antibody, a fragment of an antibody or another reagent (ligand) that binds nonrandomly with the antigen. The fluid sample of this method can comprise any body fluid which would contain *R. henselae*, for example, blood, plasma and serum. Other possible examples of body fluids include urine, sputum, mucus and the like.

In an alternative embodiment, the method of diagnosing cat scratch disease of the present invention can be such that the presence of *R. henselae* is determined by detecting the presence of an antibody from the subject which specifically binds with *R. henselae* antigen. The presence of antibody which specifically binds with *R. henselae* indicates the presence of infection by *R. henselae*. As used herein, the term "specifically binds" denotes an antibody or other ligand that does not cross react, or bind, substantially with any antigen other than the one specified, in this case, *R. henselae* antigen.

When the method of diagnosing cat scratch disease is by detecting the presence of an antibody specifically reactive (i.e. specifically binds) with *R. henselae* antigen, the step of detecting the presence of an antibody specifically reactive to *R. henselae* antigen can, for example, include the steps of contacting a fluid or tissue sample from the subject with an amount of *R. henselae* antigen that binds an antibody which specifically binds with *R. henselae* and detecting the binding of the *R. henselae* antigen with the antibody. It is expected that the antigen used will specifically bind antibodies to *R. henselae* produced in the course of *R. henselae* infection. One method of conducting such a diagnosis is illustrated in Example 2.

Detecting the reaction of the ligand with *R. henselae* antigen can be facilitated by the use of a ligand that is bound to a detectable moiety. Such a detectable moiety will allow visual detection of a precipitate or a color change, visual deletion by microscopy, or automated detection by spectrometry or radiometric measurement or the like. Examples of detectable moieties include fluorescein and rhodamine (for fluorescence microscopy), horseradish peroxidase (for either light microscopy or electron microscopy and biochemical detection), biotinstrepavidin (for light or electron microscopy) and alkaline phosphatase (for biochemical detection by color change). The detection method and detectable moiety used can be selected from the list above or other suitable examples by the standard criteria applied to such selections (14).

In the diagnostic methods of the present invention, the step of detecting the reaction of the ligand with *R. henselae* antigen can be further aided, in appropriate instances, by the use of a secondary antibody or other ligand which binds, either specifically with a different epitope or nonspecifically with the ligand or bound antibody.

In the diagnostic method which detects the presence of an antibody which specifically binds with *R. henselae* antigen, the *R. henselae* antigen can be bound to a substrate and contacted by a fluid sample such as blood, plasma or serum. This sample can be taken directly from the patient or in a partially purified form. In this manner, antibodies specific for *R. henselae* antigen (the primary antibody) will specifically bind with the bound *R. henselae* antigen. Thereafter, a secondary antibody bound to, or labeled with, a detectable moiety can be added to enhance the detection of the primary antibody. Generally, the secondary antibody will be selected for its ability to bind with multiple sites on the primary antibody. Thus, for example, several molecules of the secondary antibody can bind with each primary antibody, making the primary antibody more detectable.

Detecting methods such as immunofluorescence assays (IFA) and enzyme linked immunosorbent assays (ELISA) can be readily adapted to accomplish the detection of both *R. henselae* antigen and antibodies which specifically bind therewith. An example of an IFA protocol is provided in Example 2. The indirect immunocytochemical methods taught in Example 2 will be generally applicable for the detection of antigens or antibodies specific to an organism. An ELISA method effective for the diagnosis of cat scratch disease based on the detection of human IgG antibodies can, for example, be as follows: (1) bind the antigen (*R. henselae* antigen) to a substrate; (2) contact the bound antigen with a serum sample, containing antibodies reactive with *R. henselae* antigen, from a subject; (3) contact the above with an anti-human IgG antibody (secondary antibody) bound to a detectable moiety (e.g., horseradish peroxidase enzyme or alkaline phosphatase enzyme); (4) contact the above with the substrate for the enzyme; (5) contact the above with a color reagent; (6) observe color change in the presence of IgG antibody which specifically binds with *R. henselae* antigen. An indirect enzyme-linked immunosorbent assay (ELISA) for IgG antibodies against *R. henselae* is briefly as follows: Flat-bottomed 96-well polystyrene plates are coated with *R. henselae* or negative control antigen and allowed to incubate overnight. The next day, two-fold serial dilutions of test sera and 5 negative control sera, mouse anti-human IgG conjugated to horseradish peroxidase, and finally the substrate ABTS (2,2'-azino-di-[3-ethylbenzothiazoline sulfonate]) are added to each well sequentially. Between each step, plates are incubated for 1 hour at 37° C., and then washed 3 times with 0.1% Tween 20 in phosphate-buffered saline (pH 7.4). Dilutions of sera are considered positive when the difference in absorbance between that serum specimen when tested with *R. henselae* antigen and the negative control antigen exceeds the mean plus 3 standard deviations of the 5 negative control sera tested with both *R. henselae* and negative control antigens.

A modification of the above ELISA effective for diagnosis of cat scratch disease and bacillary angiomatosis based on the detection of human IgM antibodies can be as follows: (1) bind an anti-human IgM antibody capable of reacting with a human IgM antibody to a substrate (antibody capture); (2) contact the bound antibody with a serum sample from a subject; (3) contact the above with R. henselae antigen; (4) contact the above with a rabbit anti-R. henselae antibody; (5) contact the above with an anti-rabbit antibody bound to a detectable moiety (e.g., horseradish peroxidase enzyme); (6) contact the above with substrate for the enzyme; (7) contact the above with a color reagent; (8) observe a color change in the presence of an IgM antibody specifically reactive with R. henselae antigen. For the IgM capture ELISA, flat-bottomed 96-well polystyrene plates are coated with goat anti-human IgM antibody, followed by serial two-fold dilutions of sera including 5 negative controls, R. henselae or negative control antigens, R. henselae hyperimmune rabbit antisera, and goat anti-rabbit conjugated to horseradish peroxidase and the substrate (ABTS). Between each step, plates are incubated for 1 hour at 37° C., and then washed 3 times with 0.1% Tween 20 in phosphate-buffered saline (pH 7.4). Dilutions of sera are considered positive when the difference in absorbance between that serum specimen when tested with R. henselae antigen and the negative control antigen exceeds the mean plus 3 standard deviations of the 5 negative control sera tested with both R. henselae and negative control antigens.

Alternatively, methods such as immunoblot analysis can be readily adapted to detect the presence of R. henselae antigen and antibodies which specifically bind therewith. An example of an immunoblot analysis is provided in Example 4. The immunoblot analysis taught in Example 4 can be applicable for the detection of antigens or antibodies specific to the whole organism, or to antigens or antibodies specific to only a fragment of the whole organism. An immunoblot analysis effective for the detection of R. henselae antigen or antibodies specific to R. henselae can, for example, be as follows: (1) grow recombinant vectors containing R. henselae encoding nucleic acids in an appropriate host for expression of the recombinant nucleic acid; (2) induce the host to express the recombinant nucleic acid; (3) solubilize the host to release the polypeptide expressed by the vector; (4) electrophorese the released polypeptides on sodium dodecyl sulfate-polyacrylamide gels; (5) transfer the proteins to nitrocellulose membranes; (6) incubate the nitrocellulose membranes with serum from patients potentially infected with R. henselae; and (7) detecting the bound antigen or antibody by reacting the filters with goat anti-human IgG conjugated with horseradish peroxidase.

Another immunologic technique that can be useful in the detection of R. henselae infection utilizes monoclonal antibodies for detection of antibodies which specifically bind with R. henselae antigen. Briefly, sera from the subject is incubated with R. henselae antigen bound to a substrate (e.g. an ELISA 96-well plate). Excess sera is thoroughly washed away. A labeled (enzyme-linked, fluorescent, radioactive, etc.) monoclonal antibody is then incubated with the previously reacted antigen-serum antibody complex. The amount of inhibition of monoclonal antibody binding is measured relative to a control (no patient serum antibody). The degree of monoclonal antibody inhibition is a very specific test for a particular species since it is based on monoclonal antibody binding specificity.

A micro-agglutination test can also be used to detect the presence of R. henselae in a subject. Briefly, latex beads (or red blood cells) are coated with R. henselae antigen and mixed with serum from the subject, such that antibodies in the tissue or body fluids that specifically bind with R. henselae antigen crosslink with the antigen, causing agglutination. The agglutinated antigen-antibody complexes form a precipitate, visible with the naked eye. In a modification of the above test, antibodies which specifically reactive bind R. henselae antigen can be bound to the beads and antigen in the serum thereby detected. Other fluids of a subject can be effectively used.

In addition, as in a typical sandwich assay, the antibody is bound to a substrate and incubated with an R. henselae antigen. Thereafter, a secondary labeled antibody is bound to epitopes not recognized by the first antibody and the secondary antibody is detected.

The specific reagents and protocols for use in the detection methods described above and similar indirect immunocytochemical methods can be selected from those available in the art based on standard criteria (14).

The instant invention also provides a method of diagnosing clinical bacillary angiomatosis in a subject by detecting the presence of R. henselae antigen in the subject. The step of detecting the presence of R. henselae can be accomplished using the same protocols as taught above for the diagnosis of cat scratch disease.

Because R. quintana is also associated with BA, the instant invention also provides a method of diagnosing clinical bacillary angiomatosis in a subject by detecting the presence of R. quintana antigen in the subject. The step of detecting the presence of R. quintana can be accomplished using the same protocols as taught above for the diagnosis of cat scratch disease.

Nucleic Acids and Nucleic Acid-Based Diagnosis

In the diagnostic methods of the instant invention, the presence of R. henselae can also be determined by detecting the presence of a nucleic acid sequence specific for R. henselae. Thus, CSD can be diagnosed by detecting in a patient sample a nucleic acid that is specific for R. henselae. The nucleic acid can be detected by detecting the presence of an amplification product following polymerase chain reaction (PCR), or other routine amplification method, using species-specific primers. Alternatively, the nucleic acid can be detected by probing non-specific amplification products of PCR with a species-specific probe, as illustrated in Example 3. Additionally, a species-specific probe can be used in an in situ hybridization protocol to detect the presence of a nucleic acid sequence specific for the organism, for example in lymph node biopsy tissue from a patient suspected of having BA or CSD.

The invention also provides a method of diagnosing current or previous R. quintana infection in a subject by detecting the presence of a nucleic acid sequence specific for R. quintana by routine methods as described herein. By detecting R. quintana, bacillary angiomatosis can be diagnosed, because R. quintana is associated with BA (15).

A rapid two step method of diagnosing cat scratch disease or bacillary angiomatosis in a subject is provided. The method comprises amplifying DNA from the subject using a primer mixture consisting of SEQ ID NO:1, SEQ ID NO:2, SEQ ID NO:3 and SEQ ID NO:4. Following amplification, CSD or BA or both can be diagnosed by contacting the amplified DNA with a probe consisting of the nucleic acid of SEQ ID NO:5 and detecting the hybridization of the probe with the amplified DNA, the existence of hybridization indicating the presence of R. henselae, which is correlated with cat scratch disease, and contacting the amplified DNA with a probe consisting of the nucleic acid of SEQ ID NO:6 and detecting the hybridization of the probe with the amplified DNA, the existence of hybridization indicating the presence of R. quintana, which is correlated with bacillary angiomatosis. The steps of one example of this method are set out in detail in Example 3.

As more specifically exemplified below, a nucleic acid sequence specific for *R. henselae* can comprise nucleic acids coding for 16S ribosomal RNA subunit. Alternatively, a nucleic acid sequence specific for *R. henselae* can comprise nucleic acids coding for citrate synthase. It is apparent that a skilled artisan can apply the methods described herein for detecting the citrate synthase gene and the 16S ribosomal RNA gene to detect other nucleic acid sequences specific for *R. henselae*. Examples of other sequences specific for *R. henselae* can include the genes for heat shock protein, other antigenic proteins and certain metabolic and synthetic enzymes. The specificity of these sequences for *R. henselae* can be determined by conducting a computerized comparison with known sequences, catalogued in GenBank, a computerized database, using, for example, the computer program Gap of the Genetics Computer Group, which searches the catalogued sequences for similarities to the gene in question.

Examples 3 describes examples of nucleic acids specific for *R. henselae* and *R. quintana*. For example, a nucleic acid specific for *R. henselae* consists of the nucleotides in the nucleotide sequence defined in the Sequence Listing as SEQ ID NO:7. This gene, htrA, encodes the antigenic heat shock protein of *R. henselae*. A nucleic acid consisting of the nucleotides in the nucleotide sequence defined in the Sequence Listing as SEQ ID NO:5 is derived from SEQ ID NO:7, and is also specific for *R. henselae* (SEQ ID NO:8).

A nucleic acid specific for *R. quintana*, comprising the nucleotides in the nucleotide sequence defined in the Sequence Listing as SEQ ID NO:6 is provided. This nucleic acid is effective as a species. specific probe for detecting *R. quintana* infection as shown in Example 3. Having provided the partial nucleotide sequence for the *R. quintana* htrA gene, the remainder of the sequence can be readily obtained using standard methods, such as those described in Example 1 and elsewhere herein. Additionally, given the present invention's teaching of the sequence of the htrA gene for *R. henselae*, other sequences in the corresponding *R. quintana* htrA gene can be routinely determined to be specific for *R. quintana* merely by obtaining the full sequence and testing segments for specificity in the methods taught in Example 3.

Example 4 describes another example of a nucleic acid specific for *R. henselae*, consisting of the nucleotide sequence set forth in the Sequence Listing as SEQ ID NO:11. Immunoanalysis of this 17-kDa polypeptide suggests that this polypeptide is the immunodominant antigen of *R. henselae*, and is therefore a valuable immuno-reagent which can be used in diagnostic and prophylactic applications. Given the discovery of the nucleic acid sequence of the 17-kDa polypeptide, a skilled artisan in the relevant field can readily appreciate that nucleic acid reagents, such as primers and probes, can easily be designed for use in a nucleic acid detection system to detect the presence of a nucleic acid encoding the 17-kDa protein.

By "isolated nucleic acid" is meant the nucleic acid is separated from at least some of other components of the naturally occurring organism, for example, the cell structural components. The isolation of the nucleic acids can therefore be accomplished by techniques such as cell lysis followed by phenol plus chloroform extraction, followed by ethanol precipitation of the nucleic acids (20). It is not contemplated that the isolated nucleic acids are necessarily totally pure of non-nucleic acid components, but that the isolated nucleic acids are isolated to a degree of purification to be used in a clinical, diagnostic, experimental, other procedure such as gel electrophoresis, Southern or dot blot hybridization, or PCR. A skilled artisan in the field will readily appreciate that there are a multitude of procedures which may be used to isolate the nucleic acids prior to their use in other procedures. These include, but are not limited to, lysis of the cell followed by gel filtration or anion exchange chromatography, binding DNA to silica in the form of glass beads, filters or diatoms in the presence of high concentration of chaotropic salts, or ethanol precipitation of the nucleic acids.

The nucleic acids of the present invention can include positive and negative strand RNA as well as DNA and is meant to include genomic and subgenomic nucleic acids found in the naturally occurring organism. The nucleic acids contemplated by the present invention include double stranded and single stranded DNA of the genome, complementary positive stranded cRNA and mRNA, and complementary cDNA produced therefrom and any nucleic acid which can selectively or specifically hybridize to or encode the isolated nucleic acids provided herein.

The present invention provides isolated nucleic acids that can selectively hybridize with and be used to either detect the presence of, or amplify nucleic acids comprising the nucleotide sequences set forth in the sequence listing as SEQ ID NO:7 and SEQ ID NO:11. The stringency conditions can be those typically used in PCR protocols. In particular, an isolated nucleic acid that hybridizes with (or amplifies) the nucleic acids set forth in SEQ ID NO:7 and SEQ ID NO:11 under high stringency conditions and has at least 70% complementarity with the segment of the nucleic acid of SEQ ID NO:7 and SEQ ID NO:11 to which it hybridizes is also provided. The selectively hybridizing nucleic acids can be used, for example, as probes or primers for detecting the presence of *R. henselae* or a genetic homolog thereof that has the nucleic acid to which the primer or probe hybridizes. Thus, the invention provides a method of detecting *R. henselae* and genetic homologs thereof in a specimen and thereby detecting infection in a subject, comprising detecting the presence of a selectively hybridizing nucleic acid in a specimen from the subject, the presence of the nucleic acid indicating infection with *R. henselae* or a genetic homolog.

Also provided is a nucleic acid that selectively or specifically hybridizes with the nucleic acid of SEQ ID NO:7 under high stringency conditions and has about 85% sequence complementarity with the segment to which it hybridizes. As shown in Example 3, the htrA gene sequences of the four related Rochalimaea species demonstrate from about 85% to about 92% overall sequence identity with *R. quintana* being the most similar.

The invention also provides for a nucleic acid of at least 15 nucleotides in length which selectively hybridizes under polymerase chain reaction (PCR) conditions to the nucleic acid set forth in the Sequence Listing as SEQ ID NO:11. Since PCR is used extensively in the art, the conditions for PCR are widely known in the art and will readily be apparent to a skilled practitioner. These conditions are stated in instructions that accompany PCR machines, in standardized PCR kits provided by many biochemical reagent suppliers, as well as in many articles and standard texts.

The present invention also provides isolated nucleic acid of at least 15 nucleotides in length which specifically hybridizes with the nucleic acid set forth in the Sequence Listing as SEQ ID NO:11 under hybridization stringency conditions of 60° C. and 5× SSC (1× SSC=8.765 grams Sodium Chloride and 4.410 grams Sodium Citrate in a volume of 1 liter of $H_2O$, pH 7.0), followed by the initial washing stringency conditions of room temperature, 2× SSC and 0.1% SDS (sodium dodecyl sulfate), and two final washes under the stringency conditions of 50° C., 0.5% SSC and 0.1% SDS is provided.

The present invention therefore provides for a purified homolog of the polypeptides consisting of the polypeptides set forth in the Sequence Listing as SEQ ID NO:7 and SEQ ID NO:11. Such homolog may be obtained from other bacterial species whose genome encodes a homolog of the purified polypeptides of the present invention. For instance, Example 4 provides an immunoscreening assay in which a homolog of the 17-kDa protein of SEQ ID NO:11 can be detected. Methods used to isolate a nucleic acid encoding a bacterial or other homolog to SEQ ID NO:11 include, but are not limited to, screening the genome of a species believed to encode a homolog by nucleic acid hybridization methods or through polymerase chain reaction (PCR) techniques. Materials suitable for screening include, but are not limited to, cDNA or genomic libraries of the appropriate species cloned into lambda, cosmid, yeast, mammalian, or plasmid cloning vectors, DNA isolated and subjected to Southern blot analysis, RNA isolated and subjected to Northern blot analysis, and isolated DNA or RNA used as a template for PCR.

Also as used herein to describe nucleic acids, the terms "selectively hybridizes" and "specifically hybridizes" exclude the occasional randomly hybridizing nucleic acids as well as nucleic acids that encode heat shock proteins from other genera. The hybridizing nucleic acids can be used, for example, as probes or primers for detecting the presence of and location of a gene encoding a protein of the invention. The hybridizing nucleic acid can encode a polypeptide, and can, thereby, be placed in a suitable vector and host to produce the antigen, a functionally similar antigen, or an antigenic polypeptide fragment.

Figures 3, 4:
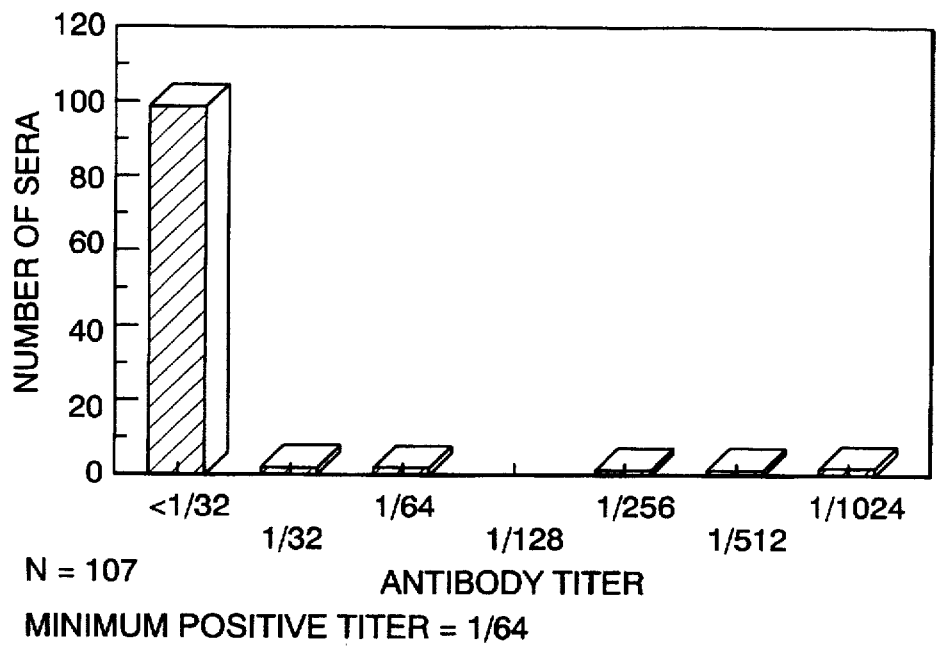
FIG. 3 shows the distribution of *R. henselae* specific antibody titers among healthy persons.
FIG. 4 shows the nucleotide sequence alignment for the three regions of the antigen gene corresponding to primers CAT1 and CAT2 and oligonucleotide probes RH1 and RQ1. The antigen gene sequences were aligned for maximal homology using only the portion corresponding to the primer and probe sequences. The sequences for *R. henselae* and corresponding base substitutions (from the *R. henselae* sequence) for other species are shown, and conserved positions are indicated with a period. The complement of PCR primer CAT2 is shown [CAT2 (C)].

The selectively hybridizing nucleic acids of the invention can have at least 80%, 85%, 90%, 95%, 97%, 98% and 99% complementarity with the segment and strand of the sequence to which it hybridizes. The nucleic acids can be at least 12 and up to 4000 nucleotides in length. Thus, the nucleic acid can be an alternative coding sequence for the antigen, or can be used as a probe or primer for detecting the presence of the nucleic acid encoding the antigen. If used as primers, the invention provides compositions including at least two nucleic acids which selectively hybridize with different regions of a nucleic acid so as to amplify a desired region. For the purpose of detecting the presence of the species-specific antigen-encoding gene, the degree of complementarity between the hybridizing nucleic acid (probe or primer) and the sequence to which it hybridizes (DNA from a sample) should be at least enough, and the sequence should be long enough, to exclude random hybridization with a nucleic acid of another species or an unrelated protein. FIG. 4 illustrates the relationship between complementarity and probe length.

The selectively hybridizing nucleic acid can also be selective for the genus, Rochalimaea, or a subset of species in the genus. For example, the primers CAT1 and CAT2 selectively amplify a product from both R. quintana and R. henselae, which can then be probed with a species specific nucleic acid. The invention provides examples of a range of selectively hybridizing nucleic acids, so that the degree of complementarity required to distinguish selectively hybridizing from nonselectively hybridizing nucleic acids under stringent conditions can be clearly determined for each nucleic acid.

"High stringency conditions" refers to the washing conditions used in a hybridization protocol. In general, the washing conditions should be a combination of temperature and salt concentration chosen so that the denaturation temperature is approximately 5°–20° C. below the calculated $T_M$ of the hybrid under study. The temperature and salt conditions are readily determined empirically in preliminary experiments in which samples of reference DNA immobilized on filters are hybridized to the probe or protein coding nucleic acid of interest and then washed under conditions of different stringencies. For example, high stringency conditions for the present selectively hybridizing nucleic acids are given in Example 3. The specific stringency conditions are readily tested and the parameters altered are readily apparent to one skilled in the art. For example, $MgCl_2$ concentrations used in the reaction buffer can be altered to increase the specificity with which the primer binds to the template, but the concentration range of this compound used in hybridization reactions is narrow, and therefore, the proper stringency level is easily determined. For example, hybridizations with oligonucleotide probes 18 nucleotides in length can be done at 5°–10° C. below the estimated $T_M$ in 6× SSPE, then washed at the same temperature in 2× SSPE (29). The $T_M$ of such an oligonucleotide can be estimated by allowing 2° C. for each A or T nucleotide, and 4° C. for each G or C. An 18 nucleotide probe of 50% G+C would, therefore, have an approximate $T_M$ of 54° C. Likewise, the starting salt concentration of an 18 nucleotide primer or probe would be about 100–200 mM. Thus, stringent conditions for such an 18 nucleotide primer or probe would be a $T_M$ of about 54° C. and a starting salt concentration of about 150 mM and modified accordingly by preliminary experiments. Tm values can also be calculated for a variety of conditions utilizing commercially available computer software (e.g., OLIGO™).

Additionally, the nucleic acids of the invention can have at least 80% homology with the coding nucleotides of SEQ ID NO:7 and SEQ ID NO:11 that are not subject to the degeneracy of the genetic code, i.e., with the non-"wobble" nucleotides (the wobble nucleotides usually being the third nucleotide in a codon) in the coding sequence. Preferably, the nucleic acids will have 90%, or more preferably, 95%, or even more preferably, 99% homology with the coding nucleotides of SEQ ID NO:7 and SEQ ID NO:11 that are not subject to the degeneracy of the genetic code.

Modifications to the nucleic acids of the invention are also contemplated as long as the essential structure and function of the polypeptide encoded by the nucleic acids is maintained. Likewise, fragments used as primers or probes can have substitutions so long as enough complementary bases exist for selective amplification.

One skilled in the art can readily obtain the nucleic acids of the present invention using routine methods to synthesize a full gene as well as shorter nucleotide fragments. For example, techniques for obtaining nucleic acids such as those provided in the Sequence Listing are specifically provided in the application. Furthermore, additional methods are provided in the art that can be utilized without significant modification. Ferretti et al. (38) and Wosnick et al. (39) show routine methods to synthesize a gene of known sequence. More specifically, Ferretti et al. teach the synthesis of a 1057 base pair synthetic bovine rhodopsin gene from synthetic oligonucleotides. The synthesized gene was faithful to the known sequence (first sentence, page 603), demonstrating the reliability of this method of gene synthesis. Additionally, Wosnick et al. teach the synthesis of a maize glutathione-transferase (GST) gene using an efficient, one-step annealing/ligation protocol. This technique also produced a complete synthetic gene with 100% fidelity, which demonstrates the routine nature of this protocol.

As described herein, the nucleic acids can be expressed to provide antigenic polypeptides of the invention.

Diagnostic Kits

The present invention further provides a kit for the diagnosis of cat scratch disease. Such a kit can be an ELISA kit and can comprise the substrate, antigen, primary and secondary antibodies when appropriate, and any other necessary reagents such as detectable moieties, enzyme substrates and color reagents as described above. The diagnostic kit of the present invention can alternatively be constructed to detect nucleic acid sequences specific for R. henselae antigen comprising the standard kit components such as the substrate and reagents such as those set forth in Example 1 for the detection of nucleic acid sequences. The diagnostic kit can, alternatively, be an IFA kit generally comprising the components and reagents described in Example 2 below. Because R. henselae infection can be diagnosed by detecting nucleic acids specific for R. henselae in tissue and body fluids such as blood and serum, it will be apparent to an artisan that a kit can be constructed that utilizes the nucleic acid detection methods taught herein. It is contemplated that the diagnostic kits will further comprise a positive and negative control test.

The particular reagents and other components included in the diagnostic kits of the present invention can be selected from those available in the art in accord with the specific diagnostic method practiced in the kit. Such kits can be used to detect R. henselae antigen and antibodies which specifically bind therewith in tissue and fluid samples from a subject and in cultures of microorganisms obtained from the tissue or fluids of a subject.

The kits of the instant invention can also be used in a method of diagnosing bacillary angiomatosis.

Vaccines

Also provided by the present invention is a vaccine comprising an immunogenic amount of a nonpathogenic Rochalimaea henselae or an immunogenically specific determinant thereof and a pharmaceutically acceptable carrier. Alternatively, the vaccine can comprise an antigenic polypeptide that specifically binds antibodies that specifically bind both R. henselae and R. quintana and a pharmaceutically acceptable carrier.

The nonpathogenic R. henselae antigen of this invention can be used in the construction of a vaccine comprising an immunogenic amount of R. henselae antigen and a pharmaceutically acceptable carrier. This R. henselae antigen can be killed, modified live or immunogenic fragments (antigenic polypeptides) of R. henselae. Alternatively, mixtures of intact R. henselae and immunogenic fragments can be used. The vaccine can then be used in a method of preventing cat scratch disease in a subject by administering the vaccine to the subject. The vaccine can also be used in a method of preventing bacillary angiomatosis in a subject by administering the vaccine to the subject. Furthermore, the fact that other disease syndromes are associated with R. henselae infection, means that such diseases can also be prevented by use of the vaccines of this invention. The prevention methods will work when the subject is a human, or likewise when the subject is a nonhuman animal, such as a cat.

For example, the vaccine can comprise an antigenic protein encoded by the nucleic acid of SEQ ID NO:7. This protein (SEQ ID NOs:7 and 8) is the R. henselae heat shock protein. The present purified heat shock protein strongly binds antibodies in rabbit serum raised against whole dead R. henselae. The homologous protein from R. quintana can also be the basis of a vaccine. To further elaborate the use of the antigen in a vaccine, standard methods can be used as described below to determine immunogenicity and immunogenic amounts.

The vaccine can also comprise the antigenic protein encoded by the nucleic acid of SEQ ID NO:11. Example 4 provides evidence that the 17-kDa protein encoded by the isolated nucleic acid of SEQ ID NO:11 is the major immunodominant antigen of R. henselae and this protein therefore provides a candidate for development of a successful vaccine for protection against R. henselae infection.

The vaccine can also comprise an antigenic polypeptide fragment encoded by a nucleic acid that selectively hybridizes with the nucleic acids of SEQ ID NO:7 or SEQ ID NO:11 under high stringency conditions and is specific for R. henselae. Because the sequences of the R. henselae and the R. quintana htrA genes share regions of high sequence similarity, a polypeptide encoded by those regions can be specific for both species and can be used in the vaccine against both CSD and BA.

The pharmaceutically acceptable carrier in the vaccine of the instant invention can comprise saline or other suitable carriers (1). An adjuvant can also be a part of the carrier of the vaccine, in which case it can be selected by standard criteria based on the particular R. henselae antigen used, the mode of administration and the subject (2). Methods of administration can be by oral or sublingual means, or by injection, depending on the particular vaccine used and the subject to whom it is administered.

It can be appreciated from the above that the vaccine can be used as a prophylactic or a therapeutic. Thus, subjects with the disease can be treated utilizing the vaccine. Further, through such vaccination the spread of disease between animals and humans can be prevented. For example, a cat or dog can be immunized, thereby preventing much of the exposure risk to humans.

Immunogenic amounts of R. henselae antigen can be determined using standard procedures. Briefly, various concentrations of a putative inactivated (nonpathogenic) immunogenically specific determinant are prepared, administered to an animal and the immunological response (i.e., the production of antibodies) of an animal to each concentration is determined.

Thus, the invention provides methods of preventing or treating an R. henselae infection and the associated disease by administering the vaccine to a subject.

Other compositions of this invention include a purified R. henselae bound to a ligand, e.g. an antibody. The term "purified" is used herein to describe antigens, antibodies and other ligands that are substantially free of other components of serum, blood or other body fluids, or other proteins associated with R. henselae in vivo.

A purified R. henselae antigen bound to a substrate and a ligand which specifically binds with R. henselae antigen are also contemplated. Such a purified ligand which specifically binds with R. henselae antigen can be an antibody. The antibody can be a monoclonal antibody obtained by standard methods. The monoclonal antibody can be secreted by a hybridoma cell line specifically produced for that purpose (14). Likewise, polyclonal antibodies which bind to R. henselae antigen are within the scope of the present invention. The polyclonal antibody can also be obtained by the standard immunization and purification protocols (14).

The antibody can be bound to a substrate or labeled with a detectable moiety or both bound and labeled. The detectable moieties contemplated with the composition of the present invention are those listed above in the description of the diagnostic methods, including fluorescent, enzymatic, and radioactive markers.

The compositions of the instant application further include an antibody reactive to a unique portion of an antibody which specifically binds with *R. henselae* antigen (primary antibody). The antibody which binds to the primary antibody is known as a secondary antibody, and can further comprise a detectable moiety. As described above, the binding of the secondary antibody to the primary antibody which specifically binds with *R. henselae* antigen facilitates detection of the binding of primary antibody with *R. henselae* antigen.

An isolated immunogenically specific determinant or fragment of *R. henselae* is also provided. The manner of obtaining such determinants is as described above for the construction of vaccines.

The following examples are intended to illustrate but not limit the invention. While they are typical of those that might be used, other procedures known to those skilled in the art may be alternatively employed.

EXAMPLE 1

Identification of *R. henselae*

A previously asymptomatic HIV-antibody positive, 40-year old man was admitted with a two month history of daily fever, extreme fatigue, anorexia, and loss of 10 Kg of weight. Five weeks after admission, blood cultures taken on the first and eighth day of hospitalization were reported positive for a Rochalimaea-like organism. With the presumptive diagnosis of trench fever, the patient was started on a 21-day course of doxycycline (100 mg, twice a day); after 48 hours he defervesced. Blood, urine, bone marrow, and bronchoalveolar lavage fluid cultures remained negative for mycobacteria and fungi. Six weeks after discontinuation of therapy, fever, anorexia, and malaise recurred. Blood cultures drawn at this time were again positive for a Rochalimaea-like organism, and treatment with doxycycline for one month (same dose as above) was reinstituted with immediate and positive response. After a second relapse of fever, the patient completed two months of doxycycline (same dose as above). Repeated blood cultures taken in the subsequent 6 months have been negative and symptoms associated with his initial infection have not recurred. The organism isolated is hereinafter designated "Houston-1 isolate", which is considered the prototype isolate of *R. henselae*. The organism is deposited with the American Type Culture Collection (ATCC, Beltsville, Md.) under Accession No. 49882.

A. Type Cultures

Two Rochalimaea isolates, representing two different recognized species, were obtained from the American Type Culture Collection (ATCC, Beltsville, Md.). *Rochalimaea quintana* (ATCC VR-358) and *R. vinsonii* (ATCC VR-152) were routinely cultivated at 35° C., 5% carbon dioxide atmosphere on tryptic soy agar, supplemented with 5% defibrinated sheep blood. *Rickettsia prowazekii*, isolate Breinl (ATCC VR-142), was cultivated in Vero cell cultures and cytoplasmic extracts containing rickettsiae were made by Regnery et al. (25).

B. Growth Characteristics

1. Isolation and cultivation of the organism from patient's blood (Houston-1 isolate).

Blood from the patient was drawn either directly into a Wampole Isostat tube (Wampole Laboratories, Cranberry, N.J.) or simply into a Vacutainer tube containing EDTA (Becton Dickinson, Rutherford, N.J.); isolates were made using both starting preparations. The organism was reisolated from frozen (−85° C.), EDTA treated blood without significant loss of titer. Primary isolations were made on commercial brain heart infusion agar (BHIA) containing 5% sheep blood (BBL, Becton Dickinson, Cockeysville, Md.), tryptic soy agar (TSA) supplemented with 5% sheep blood (BBL), and heart infusion agar (HIA) containing 5% rabbit blood (BBL). Cultures were maintained at 35° C. in a humidified incubator containing 5% carbon dioxide. Bacteriological plates were routinely examined. As noted elsewhere, the Houston-1 isolate was cultivated from blood at various times during the course of the patients disease episode including after relapse of fever following cessation of antibiotic therapy. The key to obtaining isolated cultures of *R. henselae* is to allow the culture to grow long enough for this slow-growing organism to form detectable colonies.

Blood from the febrile patient, when cultured on either commercial BHIA-sheep blood, TSA-sheep blood, or HIA-rabbit blood, yielded characteristic colonies which were visible after 9–10 days incubation. The approximate titer of colony forming organisms in the patient's blood was 30 per milliliter after recrudescence of fever following the second course of antibiotic therapy. Primary colonies were deeply invaginated (cauliflower-like), firm, adherent, and tenaciously imbedded in the surface of the agar. All original individual colonies isolated from the patient's blood had similar morphologic and growth characteristics. Close inspection of subcultured plates revealed minute colony formation by 6 days after inoculation, although clear colony morphology was not evident at this time. After multiple passages of fresh colonies, incubation time to colony visualization decreased substantially and discrete colonies could be discerned after 3 to 4 days. The invaginated colony morphology became less pronounced after multiple, relatively rapid passages. Colony growth was not limited by incubation time, and colonies continued to grow progressively larger over a period of several weeks.

Several of these latter initial growth characteristics of the Houston-1 isolate were in contrast with those noted for the ATCC Rochalimaea type strains, which typically grew relatively rapidly without any delay in passaging, had shiny, smooth colonies, and were not similarly imbedded in the agar. Likewise, although Rochalimaea species isolates obtained from ATCC proliferated rapidly on the surface of cultured cells, initial Houston-1 isolate material did not produce a similar generalized infection when inoculated on Vero cell monolayers, thus suggesting that co-cultivation with eukaryotic cells is not the method of choice for primary isolation. The Houston-1 isolate, after additional laboratory passages on solid medium (and perhaps more analogous to the ATCC type strains in terms of more extensive passage history), was not fetested for the ability to grow rapidly on eukaryotic monolayers.

After reinoculation of the organism onto either chocolate agar or TSA-sheep blood, there was no growth in air at 22° C. or 42° C. but good growth at 30° C. and 35° C. Colonies grew to slightly larger size when incubated in $CO_2$ (8%) at 35° C. than when cultured without added $CO_2$ at 35° C. Growth on subculture was also achieved on HIA-rabbit blood or TSA-sheep blood when plates were incubated in candle jars as previously described for other Rochalimaea isolates by Slater et al. (30). There was no growth observed on Sabouraud-dextrose medium. The growth characteristics of the freshly isolated Houston-1 agent contrasted with those of well-established type species of Rochalimaea. With passaging, colony morphology and speed of growth of the novel agent began to more closely resemble those of other Rochalimaea-type species. Although *R. henselae* appears to be a fastidious and slow growing organism, it can be cultivated by standard laboratory procedures. Relatively rapid growth (4 days between subculture) of the Houston-1 isolate was achieved by multiple passaging of fresh colonies shortly after they initially became visible. Semi-automated, clinical bacterial isolation procedures, which often rely on liquid media-based assays, in the absence of exogenous gaseous carbon dioxide, may not be suitable for cultivation/detection of primary Rochalimaea isolates. Moreover, such cultures are generally not maintained for an incubation period sufficient to detect growth of a primary isolate.

Preliminary attempts to-cultivate the Houston-1 isolate in stationary, liquid media did not produce turbid suspensions of individual organisms; however, the blood agar plate-derived inoculum material appeared to act as foci for growth of limited numbers of large cohesive aggregates. Reinoculation of agar-grown organisms into Bactek 660 6A or 7A bottles (Becton Dickinson, Cockeysville, Md.) did not result in sufficient growth to change the growth index as compared to uninfected controls.

2. Additional Rochalimaea isolates.

Four Rochalimaea-like isolates, previously submitted to the Centers for Disease Control and Prevention (CDC) for microbial identification were compared with the Houston-1 isolate and recognized Rochalimaea species. Two of these isolates were recovered from patients in Oklahoma, one isolate originated in a patient who apparently acquired his illness in Arkansas, and a fourth isolate which originated in San Diego County, California. This last isolate currently represents one of the first Rochalimaea isolates, that we are aware of, that has been made in recent years as well as one of the first isolates reported from an HIV-infected individual (November, 1986).

C. Clinical Biochemical Analysis Biochemical tests were performed by standard methods (16) and using the RapID ANA II System which tests for the presence of preformed enzymes (Innovative Diagnostic Systems, Inc., Atlanta, Ga.). Tests for motility included observation of growth characteristics in motility agar and direct observation of bacilli with dark field microscopy. Presence of catalase was tested for by emulsifying a colony in hydrogen peroxide and checking for the presence of microscopic bubbles formed under a cover slip. The presence of oxidase was tested for using tetramethyl-p-phenylenediamine.

Except for the production of peptidases, the Houston-1 isolate was biochemically inert when tested by typical clinical procedures. The RapID ANA II system, designed primarily for the clinical identification of anaerobic organisms by detection of specific preformed enzymes, is also useful for the identification of difficult to identify aerobic organisms. The RapID ANA II system, when used for analysis of the Houston-1 isolate, detected a limited number of enzyme-substrate cleavage reactions which included the cleavage of leucylglycine, glycine, proline, phenylalanine, arginine, and serine resulting in an identification number 000671. No known microbe is currently associated with this identification number, however, members of the genus Rochalimaea are not yet part of the commercial diagnostic database (*Rapid ID ANA II Code Compendium,* Innovative Diagnostic Systems, Atlanta, Ga., 1989). Negative clinical assays included those testing for catalase, urease, esculin hydrolysis, motility, nitrate reduction, and oxidase.

D. Staining and Morphologic Characteristics

Four day-old cultures of the Houston-1 isolate were prepared for microscopy by flooding a blood agar plate containing the colonies with phosphate-buffered saline (PBS) and then gently sweeping adherent colonies off the agar surface with a bacteriological loop. A small aliquot of this material was placed directly on a clean microscope slide, heat-fixed, and stained with Gimenez stain. Other material was fixed with glutaraldehyde and prepared for electron microscopy. Briefly, the glutaraldehyde fixed material was filtered onto a Nucleopore filter (0.2 µm pore size, Nucleopore Corp., Pleasanton, Calif.) and washed three times with Sorenson's buffer (pH 5.0). The filtered material was treated in 1% osmium tetroxide for 2 hours and again washed three times with Sorenson's buffer. The specimens were dehydrated in a graded series of increasing concentrations of ethanol (30% to 100%). The dehydrated specimens were immersed in hexamethyldisilizane (Polysciences, Inc., Warrington, Pa.) for 2 hours and then dried in a desiccator overnight. Finally, the specimens were placed on a stub, sputter coated with gold, and observed with a Philips (model 515) scanning electron microscope.

Rapidly proliferating organisms from four day-old cultures, obtained after several subpassages, stained readily with Gimenez histological stain. Organisms so stained appeared as small red bacilli, often slightly curved. Organisms obtained from older, but still quite viable colonies, resisted uptake of Gimenez stain. The material which was successfully used for light microscopy was also prepared for and observed using a scanning electron microscope. As with the Gimenez-stained material, and the observations of growth habits noted during various culturing experiments, the organisms viewed with the scanning electron microscope appeared to form cohesive aggregates, with relatively few organisms existing freely. The average size of organisms visualized was approximately 2 µm in length by 0.5 to 0.6 µm in width. All organisms observed within individual microscopic preparations, which presumably include the products of multiple generations, appeared to be relatively uniform in size.

E. Fatty Acid Analysis

Whole cell fatty acid analysis was performed on *R. henselae*, sp. nov. (Houston-1) cultures incubated at 35° C. in air and harvested after four days growth on chocolate agar. Fatty acid methyl esters were chromatographed on a Hewlett Packard series II 5890 gas chromatograph (Miller, L., T. Berger, "Bacterial identification by gas chromatography of whole cell fatty acids," Hewlett-Packard application note 228-41, Hewlett-Packard, Avondale, Pa., 1985) and identified using a computer-assisted comparison of retention times of the sample with that of a standard mixture (Microbial-ID, Newark, Del.).

The major fatty acids observed after whole cell fatty acid analysis of the Houston-1 isolate were octadecenoic acid ($C_{18:1}$, 54–56%), octadecanoic acid ($C_{18:0}$, 18–20%), and hexadecanoic acid ($C_{16:0}$, 17%). The absence of other detectable fatty acids excluded identification of almost all other bacteria except members of the genus Brucella. This fatty acid pattern was similar to that observed with *R. quintana* and other recent Rochalimaea-like isolates (30).

F. 16S rRNA Gene Sequence Analysis

1. DNA extraction, amplification and cloning.

DNA for polymerase chain reaction (PCR) amplification was extracted from pure cultures of *R. quintana*, *R. vinsonii*, and *R. henselae* (Houston-1 isolate) using sodium dodecyl sulfate (SDS)/proteinase K lysis followed by phenol/chloroform extraction as previously described (29). The resulting aqueous phase was concentrated using a Centricon 30 concentrator (Amicon Corp., Danvers, Mass.) and washed three times with 2 ml of TES (10 mM Tris, pH 8.0; 1 mM EDTA; 10 mM NaCl).

PCR amplification was performed using a thermal cycler and GeneAmp reagents (Perkin Elmer-Cetus, Norwalk, Conn.). Two pairs of "universal," degenerate primers known to amplify approximately 92% of the 16S ribosomal RNA gene, as two separate PCR products, from all eubacteria previously studied were used to prime PCR synthesis of products that were subsequently used for cloning and sequence analysis. The 5' end of each primer was modified to contain unique restriction endonuclease sites to facilitate cloning. Each sample was amplified for three cycles at: 94° C., 1 minute; 48° C., 2 minutes; 66° C., 1 minute 30 seconds, followed by 27 cycles at: 88° C., 1 minute; 52° C., 2 minutes; 68° C., 1 minute 30 seconds.

The resulting PCR products were isolated from a 1.0% agarose gel and cloned into pUC 19 (29). Clones were sequenced using double-stranded sequencing with T7 DNA polymerase (SEQUENASE, U.S. Biochemicals, Cleveland, Ohio). Each isolate was amplified, cloned, and sequenced at least twice to prevent the reading of PCR incorporation errors; if discrepancies were detected, a third, independent sequence was produced. Great care was taken not to introduce contaminating bacterial DNA into the PCR reactions using the universal primers because of their broad range of amplification. GenBank accession numbers for the respective 16S rRNA gene sequences are as follows: *R. quintana*, M73228; *R. vinsonii*, M73230; *R. henselae* (submitted as *R. americana*), M73229.

Universal primers allowed amplification of approximately 1400 nucleotides of the rRNA gene sequence as two separate PCR products. 767-base pair (bp) products, corresponding to the 5' half of the 16S rRNA gene, produced using primers EC11 and EC12 (modified versions of POmod and PC3mod primers used by Wilson et al. (26) were observed when the Houston-1 isolate, *R. quintana* and *R. vinsonii* were amplified. No product was observed when these primers were used to amplify a negative control containing no DNA template. Similarly, a 737 bp product corresponding to the 3' half of the 16S rRNA gene, produced with primers EC9 and EC10 (modified versions primers P3mod and PC5 used by Wilson et al. (40) was seen when using Houston-1 isolate, *R. quintana*, *R. vinsonii*. No PCR product was seen in the no DNA control. These PCR products were cloned and sequenced.

2. DNA sequencing.

The 16S rRNA gene sequences used for comparison and alignment were obtained by taking a consensus of three independent sequences for each cloned PCR product. The first and second sequences obtained for the Houston-1 isolate had three nucleotides in disagreement, and the first and second sequences for *R. vinsonii* had two ambiguities. In both cases a third sequence agreed with one of the two previous sequences at these ambiguous positions and was taken as the consensus. The occasional disagreement among sequences was assumed to be the result of polymerase-nucleotide incorporation errors. The entire sequence was used for alignment using the Gap program of the Genetics Computer Group. The sequence of the Houston-1 isolate was compared with 16S rRNA gene sequences on file with GenBank and showed the greatest homology with *R. quintana* (98.7%) and lesser homologies with 16S rRNA gene sequences from organisms more distantly related (Table 1).

In our laboratory, we sequenced the 16S rRNA gene from *R. quintana* (Fuller strain) and found it to differ slightly from the sequence previously reported by Weisberg et al. (35) and obtained from GenBank. Using our data, we found the 16S rRNA gene sequence from the Houston-1 isolate to be 98.7% related to *R. quintana* and 99.3% related to the *R. vinsonii*. The *R. quintana* and *R. vinsonii* sequences were found to be 98.9% related. The 0.7% 16S rRNA gene sequence divergence seen between the Houston-1 isolate and *R. vinsonii* is greater than the 0.5% divergence reported for *Rickettsia prowazekii* and *Rickettsia typhi*. These two species of Rickettsia are clearly distinct species among the order Rickettsiales, to which Rochalimaea belong.

The partial 16S rRNA gene sequence determined by Relman et al. (28) (GenBank Acc. #M59459) for the putative etiologic agent of BA was found to be identical to the corresponding portion of the 16S rRNA gene sequence obtained from the Houston-1 isolate of *R. henselae*, sp. nov. (Table 1). Partial 16S rRNA gene sequences obtained from one of the Oklahoma isolates are identical to 16S rRNA gene sequences obtained from the Houston-1 isolate. These completely homologous sequences indicate that the causative agents are one and the same species. The variation between 16S rRNA gene sequences noted between the Houston-1 isolate and other type species of Rochalimaea (Table 1) indicates that the Houston-1 isolate represents a new species within the genus Rochalimaea.

Additionally, the *R. henselae* 16S rRNA gene sequence is present in CSD skin test antigens that have been used for diagnosis of this disease for many years.

Thus, the nucleic acid encoding the 16S rRNA subunit is specific for *R. henselae* and can be compared against the 16S rRNA DNA sequences of other organisms or in test samples to detect the presence of *R. henselae*.

TABLE 1

Relatedness between the Houston-1 isolate 16S rRNA gene and various eubacteria

| Species[a] | % Homology with Houston-1 Isolate *Rochalimaea henselae* |
|---|---|
| BA-TF[b] | 100.0 |
| *Rochalimaea vinsonii* | 99.3 |
| *Rochalimaea quintana* | 98.7 |
| *Bartonella bacilliformis* | 98.2 |
| *Brucella abortus* | 94.0 |
| Cat scratch fever agent (AFIP) | 87.9 |
| *Rickettsia rickettsii* | 84.9 |
| *Ehrlichia risticii* | 84.9 |

[a]The entire 16S rRNA gene sequence (when available) was used for alignment. The *R. henselae*, Houston-1 isolate, *R. vinsonii*, and *R. quintana* sequences were determined in our laboratory, all other sequences were obtained from GenBank.
[b]Partial 16S rRNA gene sequence from Relman et al. (28).

G. Citrate Synthase Gene PCR/RFLP Analysis

Restriction-endonuclease length polymorphism (RFLP) analysis was applied to PCR-amplified DNA, which was primed with nondegenerate oligonucleotides previously demonstrated to initiate synthesis of PCR products approximately 381 nucleotides long from a portion of the rickettsial citrate synthase gene (25). Chromosomal DNA from *Rickettsia prowazekii* was used as a positive control for PCR synthesis and digestion; controls containing no DNA template were always included in PCR amplifications.

1. DNA digestion and electrophoresis.

RFLP analysis of specific genes, amplified by the PCR technique, is useful for identifying rickettsial genotypes and species. Oligonucleotides, previously demonstrated to be suitable for priming PCR amplification of a portion of the citrate synthase genes from nearly all rickettsial species, as well as from *R. quintana*, were tested for their ability to prime DNA amplification from DNA purified from the Houston-1 isolate and *R. vinsonii*. PCR products were readily produced using conditions comparable to those previously reported. Briefly, PCR amplification was accomplished in 100-μl volumes, using the protocols supplied with the GeneAmp DNA amplification reagent kit (Perkin-Elmer Cetus, Norwalk, Conn.). Typically, 1 µl of undiluted cytoplasmic extract DNA was used as PCR template. DNA amplification was done in a Perkin-Elmer Cetus DNA Thermal Cycler, using 35 cycles of denaturation (20 seconds at 95° C.), annealing (30 seconds at 48° C.), and extension (2 minutes at 60° C.).

PCR amplification of DNA was verified by rapid agarose electrophoresis of a small amount of PCR product. Restriction and endonuclease digestion was done with 20 µl of PCR reaction mixture, following standard techniques (29) and incubations were at 37° C. All restriction endonucleases were obtained from New England BioLabs, Beverly, Mass. After addition of dye-Ficoll loading mixture (29), the digested reactions were loaded on 1.5 mm thick, 8% polyacrylamide vertical gels (Bio-Rad Laboratories, Richmond, Calif.) made by standard procedures (29). Gels were run at 80 volts for 4 hours in simple vertical electrophoresis chambers (Bethesda Research Laboratories, Life Technologies, Inc., Gaithersburg, Md.). The gels were then stained with ethidium bromide prior to illumination on a UV light source (365 nm; Spectronic Corp., Westbury, N.Y.) and photographed with Polaroid type 655 P/N film (Polaroid Corp., Cambridge, Mass.).

Digested DNA fragments were separated and analyzed using standard electrophoretic protocols and methods previously described by Regnery et al. (25). The number of comigrating DNA fragments, observed between homologous PCR/RFLP digests of two or more isolates, were counted. Data from the number of comigrating DNA fragments were used to derive estimates of sequence relatedness by methods described by Upholt (32) and subsequently used by others to estimate sequence divergence between related bacteria.

All three of the uncut Rochalimaea citrate synthase PCR products were slightly larger (approximately 400 bp) than those produced for members of the genus Rickettsia (approximately 381 bp). Variation was noted between the sizes of PCR-amplified citrate synthase products obtained from different Rochalimaea isolates. PCR-amplified products were digested with seven restriction endonucleases and subjected to polyacrylamide gel electrophoresis. Obvious differences were seen in many of the digest patterns of PCR-amplified citrate synthase sequences from the various isolates; PCR/RFLP analysis allowed for rapid differentiation of other isolate genotypes.

The numbers of DNA fragments produced by digestion of the PCR-amplified, citrate synthase-specific DNA with seven restriction endonucleases are tabulated in FIG. 1, together with the number of comigrating fragments. Estimates of sequence divergence derived by numerical analysis of the percentage of comigrating fragments illustrate that all of the isolates examined have substantial inferred citrate synthase sequence divergence (6 to 11%) equalling or exceeding similar estimates for citrate synthase sequence divergence among recognized rickettsial species (e.g., 2 to 6%).

PCR/RFLP analysis clearly differentiated *R. henselae*, sp. nov., genotype from that of either *R. quintana* or *R. vinsonii*. Multiple restriction-endonuclease digests of the citrate synthase-specific PCR products from other Rochalimaea-like isolates from Oklahoma (two isolates), Arkansas (one isolate), and Southern California (one isolate) demonstrated that all of the isolates studied are identical to one another, and *R. henselae* (Houston-1 isolate), according to the PCR/RFLP methods applied herein.

It is clear that in addition to cat scratch disease and bacillary angiomatosis the disease spectrum of this organism may be variable and include a syndrome of fever and bacteremia and bacillary peliosis hepatis. Thus, the nucleic acid methods described herein can be used to detect the presence of *R. henselae* associated with these disease syndromes.

EXAMPLE 2

Serological Methods

An immunofluorescent assay (IFA) test was developed to detect antibodies specifically reactive with *R. henselae* antigen in order to begin to assess distribution and prevalence of infection, and also to help define the full spectrum of *R. henselae*-induced disease. Infectious organisms were rendered nonpathogenic by inactivation by gamma irradiation.

A. Preparation of *R. henselae* antigenic determinant

*R. henselae* bacilli cultivated on erythrocyte-enriched agar media, and then kept in solution, tend to auto-agglutinate as previously described; this clumping obstructs the production of a well dispersed IFA antigen. inhibition of auto-agglutination was achieved by co-cultivation of *R. henselae* with Vero cells to which individual Rochalimaea organisms avidly adhered. Briefly, *R. henselae* cells are cultured in liquid medium with Vero cells for 4 days. After decanting most of the liquid medium, glass beads are added to the culture flask and gently agitated in the remaining medium. This agitation with beads loosens the Vero cells and their adherent *R. henselae* cells from the flask walls. The *R. henselae* cells complexed with the Vero cells are then inactivated (rendered nonpathogenic) by gamma irradiation. Antigen and antisera were prepared for IFA testing by standard techniques.

B. Preparation of antisera (antibodies)

Briefly, the *R. henselae* antigen obtained from isolated *R. henselae* cultures and suspended in PBS is inoculated into a rabbit to cause the rabbit to produce antibodies specifically reactive with the antigen. A blood sample from the animal is taken and red blood cells are removed to obtain antisera. The serum containing *R. henselae* antibodies is then subjected to ammonium sulfate to precipitate gamma globulins (IgG) out of the antiserum.

C. IFA

The IFA of this example is conducted briefly as follows: The Vero cell-associated *R. henselae* antigenic determinant prepared above is spotted into a well of a 12-well microscope slide and a second spot of *R. quintana* (Fuller isolate) is also placed in the well. The spots are air dried and then acetone fixed for 10 minutes. Serial dilutions of the antisera being tested (e.g. 1/32, 1/64, etc., dilution endpoint) are placed in the paired wells with the antigen. The slides are then incubated in a moist chamber at 37° C. for 30 minutes and thereafter washed 3 times with PBS, rinsed with distilled water and air dried. Fluorescein labeled goat antihuman IgG is then spotted into each well, and the slides incubated, washed, rinsed and dried as above. Buffered glycerol is added to the wells for optical enhancement and the slides are then analyzed by fluorescence microscopy to detect the presence of antibody specifically reactive with *R. henselae* antigen.

In an alternative method, the *R. henselae* specific antibody purified above can be directly labeled with a detectable moiety such as fluorescein (14).

In all IFA determinations, antisera from humans with culture-confirmed *R. henselae* or *R. quintana* infections were used as positive controls.

Sera from 40 patients with suspected cat scratch disease were evaluated by IFA for reactivity with *R. henselae* antigen. Thirty-five (87.5%) patients had antibody titers to *R. henselae* that were equal to, or exceeded, 1/64 serum end-point dilution (FIG. 2). Many patients had sera with titers exceeding 1/1024. Sera collected during acute and convalescent phases of illness were available from several patients. Of five sets of paired sera that had different titers and included at least one specimen with a titer equal to, or exceeding, 1/64, three demonstrated four-fold rises or falls in antibody titer. Three additional paired sets of sera could not be evaluated for change in titer because both sera had antibody specifically reactive with R. henselae antigen of, or exceeding, a titer of 1/1024 (the maximum titer assayed). Eight of the sera with a titer of, or exceeding, 1/64 also had low antibody titers to R. quintana which did not exceed 1/32. In each of these sera, the titer of antibody specifically reactive with R. henselae exceeded the titer to R. quintana by at least four-fold.

107 sera collected from persons who identified themselves as healthy individuals were obtained from a contract vendor (Worldwide Biologics, Cincinnati, Ohio). When these sera were tested by IFA for antibody reactive with R. henselae and R. quintana, 101 (94%) had titers less than 1/64 (FIG. 3). Of the six sera that had antibody titers to R. henselae antigen equal to or greater than 1/64, three had considerably elevated antibody titers (i.e., 1/512 and 1/1024). Antibody titers to R. quintana exceeding 1/16 were not detected among the serum donors.

Sera from persons with a variety of diseases were evaluated for the presence of possible antibodies specifically reactive with R. henselae. Titers less than or equal to 1/64 were detected in two of ten persons with brucellosis, however, the two low level positive serologic responses did not correlate with increasing titers of antibody to Brucella abortus as detected by microagglutination. One of three sera from patients with Lyme disease had a titer of 1/64 to R. henselae. Sera from patients with tularemia and sera from patients with Yersinia entercolitica infections did not show antibody titers to R. henselae that were in equal to or greater than 1/64. A number of other reference human antibodies used as reagents in diagnostic kits were evaluated with the R. henselae IFA test. None of these sera showed a titer of antibody for R. henselae at or above 1/64. The reference sera included human antisera to: Mycoplasma pneumoniae, Treponema pallidum, Coxiella burnetii, Ehrlichia chaffeensis, chlamydia group, spotted fever group rickettsiae, typhus group rickettsiae, varicella zoster, influenza type A, adenovirus, dengue virus type 2, herpes simplex, coxsackievirus group A, poliovirus type 2, cytomegalovirus, rubella, human immunodeficiency virus type I, as well as alpha-fetoprotein and rheumatoid factors.

Sera containing high-titered human antibody specifically reactive with R. henselae and antibodies for R. quintana did not react with "A. felis" antigen in the IFA test. Hyperimmune rabbit antisera and monoclonal antibodies directed against "A. felis" antigen were not reactive with R. henselae whole cell antigen.

High titered R. quintana antibody (1/1024 dilution endpoint) obtained from a human volunteer infected with R. quintana (Fuller isolate) yielded no discernable reaction with R. henselae antigen (<1/16 dilution endpoint). Similarly, minimal (<1/32 dilution endpoint) R. quintana antibody titers were noted when high titered (e.g. >1/1024 dilution endpoint) serum was used from a culture positive R. henselae-infected patient.

Thus, it is seen that the human serologic responses to R. henselae and R. quintana (Fuller isolate) antigens, as assayed in the IFA test, are species-specific and it is unlikely that the antibody reactions observed with R. henselae antigen were due to antigenic stimulation by any species other than R. henselae.

There was a low prevalence of significantly elevated levels of antibody specifically reactive with R. henselae found among apparently healthy serum donors, indicating that R. henselae infection may be relatively common. Out of 40 patients clinically diagnosed with cat scratch disease, 35 (87.5%) had sera antibody titers to R. henselae antigen that equaled or exceeded 1/64 and several paired sets of sera showed four-fold changes in titer. This method of detecting R. henselae antigen or antibodies specifically reactive therewith provides a useful diagnostic tool for identification of patients with cat scratch disease and thereby reduces reliance on clinical diagnosis alone, use of non-pharmaceutically approved CSD skin test antigen preparations, and need for surgical biopsy.

The method of diagnosing cat scratch disease exemplified herein can be applied equally effectively to the diagnosis of bacillary angiomatosis, because an etiologic agent of both diseases is R. henselae. Also, because R. henselae infection is associated with other disease syndromes, such as a syndrome of fever and bacteremia and bacillary peliosis hepatis, the serological, immunocytochemical, cytological and nucleic acid detection methods described above can be effectively used to diagnose these diseases.

EXAMPLE 3

Detection of R. henselaea and R. quintana by PCR
A. Bacterial Strains

All strains of bacteria used for evaluating the specificity of the PCR and hybridization assay are listed in Table 2. Rochalimaea spp. were grown on heart infusion agar plates supplemented with 5% defibrinated rabbit blood (HIA-RB) (BBL, Rockville, Md.) incubated for 3 to 5 days at 34° C. in the presence of 5% $CO_2$. Bartonella bacilliformis was cultivated on HIA-RB for 6 to 8 days at 28° C. without supplemental $CO_2$. A. felis was grown on charcoal-yeast extract agar plates (Carr-Scarborough Microbiologicals, Decatur, Ga.) for 2 to 3 days at 32° C. without $CO_2$.

TABLE 2

Isolates whose DNA was used for specificity testing of the PCR primers and oligonucleotide probes.

| | | | | Probes | |
|---|---|---|---|---|---|
| ID | bacteria | source (ref.) | PCR | RH1 | RQ1 |
| Houston-1* | R. henselae | HIV+ patient (23) | + | + | − |
| San Ant-1 | R. henselae | HIV− patient (18) | + | + | − |
| San Ant-2 | R. henselae | CSD patient (9) | + | + | − |
| San Ant-3 | R. henselae | CSD patient (9) | + | + | − |
| San Diego-2 | R. henselae | San Diego, HIV+ | + | + | − |
| OK88-64 | R. henselae | HIV+ patient (34) | + | + | − |
| OK88-712 | R. henselae | HIV− patient (34) | + | + | − |
| OK89-674 | R. henselae | HIV− patient (34) | + | + | − |
| OK89-675 | R. henselae | HIV− patient (34) | + | + | − |
| OK90-615 | R. henselae | HIV− patient (34) | + | + | − |
| OK90-782 | R. henselae | HIV+ patient (34) | + | + | − |
| CAL-1 | R. henselae | San Diego, HIV+ | + | + | − |
| Fuller* | R. quintana | ATCC VR358 | + | − | + |
| OK90-268 | R. quintana | HIV+ (34) | + | − | + |
| SH-PERM | R. quintana | Russia | + | − | + |
| D-PERM | R. quintana | Russia | + | − | + |
| F9251* | R. elizabethae | heart valve (8) | −* | − | − |
| RV* | R. vinsonii | ATCC VR152 | − | − | − |
| KC584 | B. bacilliformis | ATCC 35686 | − | − | − |
| BV* | A. felis | ATCC 53690 (7) | − | − | − |

*The 414bp PCR product was not observed. A larger product of approximately 1300 bp was amplified from R. elizabethae that failed to hybridize with either the RH1 or RQ1 probe.
*Denotes type strain for the species.

B. Clinical Samples

Twenty-five samples from patients clinically diagnosed with CSD were used for evaluating a further example of a PCR assay (Table 3). All CSD cases were clinically diagnosed by the physician and had regional lymphadenopathy and cat contact in the absence of other obvious diagnosis. All patients whose samples were used met this definition except patient #16 (Table 3), who had no known history of cat contact. Sixteen of these were fresh lymph node biopsy specimens and nine were lymph node aspirates. In addition, five lymph node aspirates from non-CSD patients, from whom other organisms were isolated, were included as negative controls. Likewise, three lymph node biopsies from non-CSD patients were used as additional negative controls. Serology was performed on some patients (when serum was available) by the indirect fluorescence antibody test illustrated in Example 2.

Fresh frozen tissue from both lymph node biopsy specimens and lymph node aspirates were suitable samples.

TABLE 3

Information and PCR/dot-blot results on CSD patients.

| patient | state | sample | PCR-CSD | hybridization with probe: RH1 | RQ1 | serology[a] |
|---|---|---|---|---|---|---|
| 1 | MA | aspirate | + | + | − | + |
| 2 | MA | biopsy | + | + | − | + |
| 3 | MO | biopsy | + | + | − | + |
| 4 | FL | biopsy | + | + | − | + |
| 5 | FL | biopsy | + | + | − | + |
| 6 | OH | biopsy | + | + | − | + |
| 7 | SC | biopsy | − | − | − | + |
| 8 | NJ | biopsy | + | + | − | + |
| 9 | VA | biopsy | − | − | − | + |
| 10 | NJ | biopsy | + | + | − | + |
| 11 | NJ | biopsy | + | + | − | + |
| 12 | PA | biopsy | + | + | − | + |
| 13 | MA | aspirate | + | + | − | + |
| 14 | WV | biopsy | − | − | − | + |
| 15 | ME | biopsy | + | + | − | + |
| 16 | NC | biopsy | + | + | − | + |
| 17 | WA | biopsy | + | + | − | + |
| 18 | MA | aspirate | + | + | − | + |
| 19 | GA | biopsy | − | − | − | − |
| 20 | TN | aspirate | + | + | − | + |
| 21 | TN | aspirate | + | + | − | + |
| 22 | TN | aspirate | + | + | − | + |
| 23 | FL | aspirate | + | + | − | ND |
| 24 | TN | aspirate | + | + | − | ND |
| 25 | VA | aspirate | + | + | − | ND |
| 26 | TN | aspirate | −[b] | − | − | ND |
| 27 | TN | aspirate | −[b] | − | − | ND |

[a]serology was performed by the indirect fluorescence antibody test as previously described (23). An anti-Rochalimaea titer of 1:64 or higher was considered positive.
[b]Two representative negative controls of non-CSD cases from which other bacteria were isolated.

C. DNA Extraction

DNA was extracted from bacterial cells, lymph node tissue, or lymph node aspirates using modifications of a procedure previously described (4). Briefly, bacterial growth harvested from approximately ⅛th of a standard size (85 mm) HIA-RB plate was resuspended in 300 µl of PCR diluent (10 mM Tris, 10 mM NaCl, 1 mM EDTA, pH 8.0). For lymph node tissue, samples (approximately 100 mg) were dispersed using a disposable homogenizer in minimal essential medium, (0.5 ml) and 50 to 100 µl of this homogenate was diluted to 300 µl with PCR diluent. Lymph node aspirates (50 to 100 µl) were resuspended and diluted to 300 µl with PCR diluent. The samples were then made 1.0% sodium dodecyl sulfate (SDS) and proteinase K was added to a final concentration of 100 ng/µl, and the samples were incubated for 2 hours at 55° C. After incubation, the lysates were extracted three to four times with a 50:50 mixture of buffer saturated phenol and chloroform/isoamyl alcohol (24:1). The resulting aqueous supernatant was diluted to 2.0 ml with PCR diluent, filtered through a Centricon 30 filter (Amicon, Danver Mass.) and washed twice more with 2.0 ml aliquots of PCR diluent. The subsequent filter retentate (average volume of 40 µl) was collected and used as template for the PCR. For every DNA extraction run, a reagent blank was processed exactly as described above to ensure that all extraction buffers and reagents were not contaminated with Rochalimaea DNA.

D. PCR Primer and Hybridization Probe Design

A library of R. henselae DNA was constructed in the vector lambda ZapII (5). The library was screened with either a pool of eight monoclonal antibodies or rabbit hyperimmune serum for expression of antigenic proteins. A clone expressing a 60-kilodalton antigen reactive with rabbit anti-R. henselae serum has been isolated and the gene sequenced (6)(GenBank Accession L20127). (SEQ ID NO:7) The deduced amino acid sequence was shown to have 37% sequence homology (over the entire sequence) with the htrA locus described from Escherichia coli (17). Primer pair CAT1 5' GATTCAATTGGTTTGAA(G and A)GAGGCT 3' (SEQ ID NOs:1 and 2) and CAT2 5'TCACATCACCAGG(A and G)CGTATTC 3' (SEQ ID NOs:3 and 4) (FIG. 4), which defines a 414 base pair (bp) fragment from both R. henselae and R. quintana, was used for PCR amplification. Twenty-base pair oligonucleotide probes RH1 (SEQ ID NO:5) and RQ1 (SEQ ID NO:6) (FIG. 4) were used as species-specific hybridization probes.

Partial nucleotide sequences (150–200 nucleotides) of the same gene from the other three species of Rochalimaea were obtained using conserved PCR primers. PCR with the primer pair htr5 (5' AATCTAGATTGCTTTCGCTATTC-CGGC 3' (SEQ ID NO:8)) and htr6 (5' AAGGATC-CATTTGTTCGCACTTGTAGAAG 3' (SEQ ID NO:9)) resulted in the amplification of a 650 base pair product from each of the four Rochalimaea species. The 150–200 base pair sequences of the other three species obtained from these amplification products were found to be 85 to 92% conserved with the R. henselae sequence. No evidence of the present htrA gene was found in B. bacilliformis, an organism phylogenetically closely related to Rochalimaea spp. (21, 27). This observation is interesting since B. bacilliformis does not grow at elevated temperatures, a trait which in part may be do to the lack of a functional htrA gene product.

E. PCR Assays

DNA prepared from bacteria, fresh lymph node tissue, or lymph node aspirates was used as template for the PCR assays. Five µl portions of the template DNA (undiluted and diluted 1:10) extracted from the clinical samples was used for each PCR assay. The approximate concentration of DNA extracted from bacterial isolates was determined by agarose gel electrophoresis next to known quantities of standard DNA. Diluted bacterial DNA (approximately 1 ng) was used for the initial determination of primer specificity. For subsequent PCR on clinical samples, 10 pg (in 10 µl) of DNA extracted from either R. henselae or R. quintana was used as a positive control and the DNA extraction blank and water (10 µl each) were used as a negative controls. The GeneAmp reagent (Perkin-Elmer Cetus, Norwalk, Conn.) kit was used for all PCR assays. Degenerate primer pair CAT1 and CAT2 was used to prime the polymerization reactions. The primer mixture included about equal amounts of the R. quintana (SEQ ID NOs:2 and 4) and R. henselae (SEQ ID NOs. 1 and 3) primer sequences. Amplification was accomplished by predenaturing for 5 minutes at 94° C. followed by 35 cycles of 94° C., 30 seconds; 50° C. for 60 seconds; and 70° C. for 45 seconds in a model 9600 thermal cycler (Perkin-Elmer). Ten microliters from each PCR assay was electrophoresed through a 1.2% agarose gel, stained with ethidium bromide, and photographed. The presence of a 414 bp band was considered positive. Each sample of DNA extracted from the clinical specimens was also amplified with primer pair GHPCR1 and GHPCR2 (36). This primer pair amplifies a 422 bp fragment from a conserved region of the human growth hormone gene and serves as a positive control for successful extraction of amplifiable DNA. DNA extracts from clinical samples that failed to amplify with primer pair GHPCR1 and GHPCR2 were excluded from further study.

F. Specificity of the PCR Assay

Under the conditions described above and with purified template DNA, all 12 *R. henselae* isolates and all four *R. quintana* isolates yielded the predicted 414 bp fragment of amplified DNA (Table 2). No amplification products were observed for *R. vinsonii*, *B. bacilliformis*, and *A. felis*. *R. elizabethae* was amplified with this primer pair, but the product was much larger (approximately 1300 bp) than the 414 bp predicted for *R. henselae* and *R. quintana*. Thus, the 414 bp PCR product appears to be specific for *R. henselae* and *R. quintana*. A PCR product of approximately 50 to 60 bp was occasionally observed in the no DNA control and presumably corresponds to primer dimer.

The degenerate primers CAT1 and CAT2 appear to be well conserved within the isolates of *R. henselae* and *R. quintana*.

Greater success was obtained using aspirates (%, 100% positive) than biopsies ($^{12}/_{16}$, 75% positive), probably because of the inherent difference between nodes which are fluctuant and thus can be aspirated and those which are not. Difficulty is encountered in standardizing the amount of DNA extracted from either lymph nodes or aspirates. Since we utilized a total lysate procedure, both RNA and DNA was obtained and measuring the lysates absorbance would be a poor indicator of DNA concentration. Accordingly, we used each sample of template undiluted and at a 1:10 dilution for amplification.

G. Dot-blot Hybridizations

To confirm the identity of the PCR products and to allow differentiation of products amplified from *R. henselae* and *R. quintana* templates, a dot-blot hybridization assay was performed on the PCR products amplified from the bacteria listed in Table 2. Oligonucleotide probes RH1 and RQ1 were used for this purpose. RH1 and RQ1 were nonisotopically labeled by transfer of a digoxigenin-ddUTP nucleotide to the 3' end of each oligonucleotide by means of terminal transferase using Genius 5 labeling kit (Boehringer Mannheim, indianapolis, Ind.). For the dot-blot hybridization assays, 5 µl of each PCR product was denatured for 10 minutes by the addition of 0.5 µl of 4M NaOH containing 100 mM ethylene diamine tetraacetic acid. One-microliter aliquots were spotted onto each of two nylon membranes (Boehringer Mannheim) and the DNA was cross-linked to the nylon by UV irradiation (Stratalinker, Stratagene, La Jolla, Calif.). The nylon membranes were then blocked for 1 hour at 62° C., using standard prehybridization solution from the Genius 7, luminescent detection kit (Boehringer Mannheim). Standard hybridization solution was 5× SSC (1× SSC=0.15M NaCl and 0.015M sodium citrate) containing 0.1% N-laurylsarcosine, 0.02% SDS, and 1.0% blocking reagent (Boehringer Mannheim). Hybridization was then performed at 62° C. ($T_M$-8° C. for both probes) for 1 hour in fresh prehybridization solution containing either probe RH1 or RQ1 at a concentration of 2 pmol/ml. The hybridized membrane was then washed twice for 15 minutes each in 2× SSC containing 0.1% SDS at room temperature, followed by two washes of 15 minutes each at 52° C. in 0.5× SSC with 0.1% SDS. The hybridized filter was then blocked, reacted with alkaline phosphatase conjugated antibody, washed, and soaked in Lumigen PPD chemiluminescent substrate according to the manufacturer's directions (Genius 7 kit, Boerhinger Mannheim). The resulting filter was exposed to X-ray film for 5 to 20 minutes and the film was developed.

H. Specificity of Dot-Blot Hybridization Assay

PCR products amplified from all 12 isolates of *R. henselae* hybridized with probe RH1. PCR products from all four isolates of *R. quintana* hybridized only with probe RQ1. Neither probes RH1 or RQ1 hybridized to the PCR products from *R. elizabethae*, *R. vinsonii*, *B. bacilliformis*, or *A. felis*. Thus, the dot-blot hybridization assay allows differentiation between PCR products amplified from *R. henselae* and *R. quintana*.

The oligonucleotide probes (RH1 and RQ1) while being species-specific, appear to be well-conserved within the species.

I. PCR and Dot-Blot Assays on Clinical Samples

To evaluate the PCR and dot blot assays for detection of *R. henselae* and *R. quintana* in clinical samples, these techniques were applied to 16 samples of fresh lymph node tissue and 9 aspirates from CSD cases. Twenty-one of 25 samples (84%) produced the 414-bp product that is characteristic of *R. henselae* or *R. quintana* (Table 3). Representative PCR products obtained from lymph node biopsy samples and a lymph node aspirates of suspect CSD patients were electrophoresed. Two samples produced the characteristic 414 bp band only when the template DNA was diluted 1:10 before amplification. Typical of these samples is #9, the amplification of which appears to be inhibited by large amounts of leukocyte DNA. When the sample containing the template DNA was diluted 1:10 prior to amplification, the 414 bp band was clearly produced. The characteristic 414 bp fragment was not amplified from any of the eight lymph node tissue samples from non-CSD cases or from DNA extraction blanks.

To confirm the identity of the PCR products amplified from the clinical samples and to sort those infections caused by *R. henselae* from those caused by *R. quintana*, a dot-blot hybridization was performed using species-specific probes RH1 and RQ1. The PCR products from all 21 samples that amplified to produce the characteristic 414 bp fragment hybridized with *R. henselae*-specific probe RH1. Conversely, none of these samples hybridized with *R. quintana*-specific probe RQ1. Thus, all the PCR positive samples studied here, from suspected CSD patients in 11 different states (Table 3), appear to be associated with *R. henselae* and not *R. quintana*. None of the samples that failed to amplify the 414 bp fragment as determined by agarose gel electrophoresis hybridized with either probe.

The present results indicate that, unlike BA and other opportunistic infections seen among AIDS patients that may be caused in some cases by *R. henselae* and in others by *R. quintana*, CSD appears to be caused primarily (or perhaps exclusively) by *R. henselae*.

The 84% positive samples from suspect CSD cases for the PCR assay described here is virtually identical to the 84% and 88% positive observed by serologic means on two separate groups of samples from suspect CSD patients (24, 37). Twenty-two of the samples from CSD cases tested herein by PCR were also tested by serology (Table 3). Twenty-one of these (95%) had an IFA titer of 1:64 or greater. Thus, three samples collected from seropositive individuals were negative by the PCR assay. This apparent discrepancy may be due in part to the lack of intact organisms in the lymph nodes from patients in the later stages of CSD. In fact Gerber et al have postulated that the lingering cell-mediated immune response and resulting granulomatous reaction rather than bacterial invasion may be the major pathogenic mechanism of CSD (13). Alternatively, there may be inhibitors of PCR present in lymph node tissue that preclude attaining optimal sensitivity of the assay.

The PCR assay offers the advantage of early diagnosis since it is not dependent on the patient mounting a detectable humoral immune response. In addition, the PCR assay differentiates *R. henselae* from *R. quintana* infections. A rapid and specific test for CSD affords the clinician an alternative to culture or serology for laboratory confirmation of the diagnosis, thereby permitting the clinician to rule out malignancies such as lymphoma and to consider antibiotic therapy. Although the efficacy of antibiotics in treating CSD remains uncertain, successful treatment with four antibiotics (rifampin, ciprofloxacin, trimethoprim-sulfamethoxazole, and gentamicin sulfate) has been reported (19), and in vitro, *R. henselae* is sensitive to many common antibiotics (9).

EXAMPLE 4

Identification of Antigenic Fragments of *R. henselae*

A library of *Rochalimaea henselae* DNA was constructed in the cloning vector lambda ZapII and screened for expression of antigenic proteins using a pool of sera from patients diagnosed with cat-scratch disease (CSD) and who had antibodies to Rochalimaea as determined by the indirect fluorescent antibody (IFA) assay. Ten immunoreactive phage were subcloned as recombinant plasmids by in vivo excision. All ten recombinants expressed a protein of approximately 17-kilodaltons (kDa) when examined by immunoblot analysis using the pool of human sera. Restriction endonuclease digestion of each of the ten recombinant plasmids indicated seven different profiles, suggesting that cloning bias was not the reason for repeatedly isolating clones expressing the 17-kDa antigen. The gene coding for the 17-kDa antigen was sequenced and shown to code for an open reading frame of 148 amino acids and a predicted molecular mass of 16,893 Daltons. (SEQ ID NO:11) The amino terminus of the deduced amino acid sequence was hydrophobic in nature and similar in size and composition to signal peptides found in Gram-negative bacteria. The remainder of the deduced amino acid sequence was more hydrophilic and may represent surface-exposed epitopes. Further subcloning of the 17-kDa antigen as a biotinylated fusion protein in the expression vector PinPoint Xa-2 resulted in a 30-kDa protein that was highly reactive on immunoblots with individual serum samples from patients with CSD. The agreement between reactivity with the 30-kDa fusion protein on immunoblot analysis and results obtained by the IFA assay was 92%, n=13 for IFA positive and 88%, n=9 for IFA negative. The recombinant expressed 17-kDa protein should be of value as an antigen for serologic diagnosis of CSD and Rochalimaea infections and warrants further study in attempts to develop a subunit vaccine to prevent long-term infection by Rochalimaea in cats, and the potential for further spread of the organism to humans.

A. Cultivation of Rochalimaea

Rochalimaea strains were grown on heart infusion agar supplemented with 5% defibrinated rabbit blood (BBL, Cockeysville, Md.). The Houston-1 strain of *R. henselae* and the Fuller strain of *R. quintana* were used for all experiments described in this example. Cultures were incubated at 34° C. in the presence of 5% $CO_2$. After growth was sufficient (3 to 4 days) the bacterial cells were harvested with sterile applicators and suspended in TE buffer (10 mM Tris pH 8.0, 1 mM EDTA). Bacteria were concentrated as needed by centrifugation. Bacterial cells were then frozen and stored for subsequent immunoblot analysis or the DNA extracted as outlined below.

B. Construction of *R. henselae* DNA Library

A lambda phage library of *R. henselae* DNA was prepared using the lambda ZAPII vector (Stratagene, Torrey Pines, Calif.) using a novel method developed specifically for constructing DNA libraries of A-T rich organisms (5). Total (chromosomal and extrachromosomal) DNA was isolated from the Houston-1 strain of *R. henselae* by lysis of the bacterial cells with 1.0% SDS in the presence of proteinase K (100 ng/µl) at 55° C. for 90 minutes. The resulting lysate was extracted with a 50:50 mixture of phenol and chloroform 4 times. The nucleic acids were precipitated from the aqueous phase by the addition of sodium acetate to 0.3M and 2½ volumes of absolute ethanol. The precipitate was collected by centrifugation and resuspended in TE buffer with 10 ng/µl of ribonuclease A. The extracted DNA was digested with the restriction endonuclease EcoRI under conditions that promote enzymatic activity (star activity). This star activity is less specific and hence more random than the cleavage with EcoRI under normal conditions. EcoRI star activity generated DNA fragments are efficiently cloned into EcoRI-cleaved vectors (5). The resulting DNA was size selected for fragments 3–8 kilobase pair in length by electrophoresis through a 0.7% agarose gel and purification by adsorption to glass milk (GeneClean, Bio101, Vista, Calif.). The purified and sized DNA ligated to EcoRI digested alkaline phosphatase-treated lambda ZAPII vector. The recombinant phage concatamers were then packaged into lambda particles using a Gigapack packaging extract (Stratagene, Torrey Pines, Calif.). After packaging, an aliquot of the library was titered and assayed for the percentage of recombinants by plating with *Escherichia coli* strain XL1 (Stratagene, Torrey Pines, Calif.) on NZY agar plates. The library was amplified by plating the entire packaged ligation reaction and collected by overnight diffusion of the recombinants into phage dilution buffer (10 mM Tris pH 8.0, 10 mM $MgCl_2$, 0.1% gelatin).

C. Immunoscreening of recombinant clones

For screening of recombinant phage for immunoreactivity with human sera, lambda phage clones were plated at a density of approximately 30,000 per 150 mm plate of NZY agar. After incubation for 3–4 hours at 42° C. (until the plaques were barely visible) the plates were overlaid with nitrocellulose filters impregnated with 1 mM isopropyl β-D-thioglactopyranoside (IPTG) and the incubation continued for an additional 3 hours at 37° C. The filters were then washed twice in Tris-buffered saline containing 0.1% Tween 20, pH 8.0 (TBST), and blocked with TBST containing 5.0% dehydrated skim milk (Difco, Detroit, Mich.) for one hour at room temperature. The filters were then reacted with a pool of serum samples (diluted 1:300 in TBST with 5% skim milk) from patients clinically diagnosed with CSD for two hours. This pool of serum samples consisted of 10 individual sera from patients diagnosed with CSD and that were shown to have a titer of 1:1024 or greater as determined by the indirect fluorescent antibody (IFA) assay for Rochalimaea performed as previously described (42). The filters were then washed four times with TBST and bound antibody detected by reacting the filters with goat anti-human IgG conjugated with horseradish peroxidase (diluted 1:3000 in TBST with 5% skim milk) for one hour at room temperature. The filters were washed four times in TBST and the color developed using TMB membrane substrate (Kirkegaard and Perry, Gaithersburg, Md.).

D. Rescue and analysis of recombinant phagemids

After several rounds of plaque purification of immunoreactive recombinant phage, the isolated phage plaques were subcloned from the lambda phage recombinants into pBluescript-derived plasmids according to the directions of the manufacturer (Stratagene, Torrey Pines, Calif.). Briefly, by superinfecting lambda recombinant-infected *E. coli* XL1 MRF' cells with R408 helper phage, the pBluescript portion of the lambda ZAPII vector containing the inserted Rochalimaea DNA was rescued. These recombinant phagemids were then used to infect XL1 MRF' cells, where they replicate as plasmids upon selection with ampicillin. This procedure results in colonies harboring pBluescript-derived recombinant plasmids with Rochalimaea DNA inserts. These recombinant plasmids were used for further analysis and sequencing of DNA and for immunoblot analysis of plasmid encoded Rochalimaea proteins expressed in *E. coli*.

E. Immunoblot analysis

To analyze human antibody response to individual antigens, whole cell lysates of Rochalimaea and *E. coli* recombinants were subjected to SDS-PAGE and immunoblot analysis. Rochalimaea was grown as described above. *E. coli* recombinants were grown in LB broth containing 100 ug/ml of ampicillin at 37° C. with shaking to mid-log phase and 1 mM IPTG was added. incubation was continued for an additional 2 hours at 37° C. with shaking and cells were collected by centrifugation. The resulting cell pellets were solubilized in sample buffer (2% SDS, 50 mM Tris pH 8.0) for SDS-PAGE for 5 minutes at 100° C.

Solubilized Rochalimaea and *E. coli* recombinant cell proteins were electrophoresed through 8–16% gradient SDS-PAGE mini gels (Novex, San Diego, Calif.). The resulting cell proteins were stained directly with Coomassie brilliant blue or transferred to nitrocellulose using a mini-transfer apparatus (Bio-Rad, Richmond, Calif.). After electro-transfer of proteins to nitrocellulose, the resulting filters were reacted with antisera and treated as described in the "immunoscreening of recombinant phage clones" section of this Example.

F. Sequencing of phagemid DNA

Plasmid DNA from recombinants was prepared from mini-preps by alkaline lysis. The resulting plasmid DNA was used for restriction endonuclease digestion and directly for double-stranded plasmid sequencing by the dideoxy chain termination method. Plasmids were sequenced using alkaline denaturation by the method of Zhang (44) followed by chain extension and termination with T7 DNA polymerase (Sequenase, US Biochemical) using $^{35}$S dATP. Sequenced DNA was electrophoresed through a denaturing 6% acrylamide-urea gel and the resulting gel was fixed with 10% acetic acid and 5% methanol. After vacuum drying, the gel was exposed to X-ray film for approximately 12–24 hours and developed. Plasmids were sequenced with the M13 forward or reverse primers or using primers that were synthesized from the *R. henselae* insert as the sequencing progressed. To further localize the 17-kDa antigen gene and for additional sequencing, restriction fragments were subcloned into pUC19 by standard methods (20) and examined for expression by immunoblot analysis.

G. Construction of fusion protein

Gene fusion techniques were used to confirm the identity of the putative 17-kDa antigen gene and allow for it's optimal expression in *E. coli*. PCR primers from the putative 17-kDa antigen gene sequences were designed that contained a HindIII site (underlined) on the 5' end primer (5' AA AAGCTTGAAAAAATATAGCTTAGTCAC 3', SEQ ID NO:13) and a BamHI site (underlined) on the 3' end primer (5' AAGGATCCAGAAATGCTCTCAAAC 3', SEQ ID NO:14). These unique restriction sites facilitate directional and in-frame cloning. DNA from the Houston-1 strain of *R. henselae* was amplified through 35 cycles of 94° C. for 1 minutes, 48° C. for 2 minutes, and 68° C. for 1.5 minutes using GeneAmp reagents and Taq polymerase and a thermal cycler (Perkin Elmer, Norwalk, Conn.). The resulting PCR product was cleaved with HindIII and BamHI, gel-purified and ligated to the expression vector PinPoint Xa-2 to produce a fusion of the antigen with the 13-kDa biotinylation tag sequence of the vector (Promega, Madison, Wisc.). This tag sequence has been engineered by the manufacturer to permit rapid purification of biotinylated fusion proteins away from other *E. coli* cell proteins. There are also endoprotease cleavage sites to permit cleavage of proteins from the tag sequence. The ligation mixture was used to transform *E. coli* strain XL-1 MRF' (Stratagene, Torrey Pines, Calif.). Potential clones were examined by restriction endonuclease analysis to confirm the presence of the correct size insert. Clones containing the correct size insert were grown to early log-phase in LB broth and induced with 1 mM IPTG and growth was allowed to continue an additional two hours. The *E. coli* cells were collected by centrifugation and examined for the expression of biotinylated fusion proteins by immunoblot analysis using streptavidin conjugated to horseradish peroxidase. Clones expressing the biotinylated fusion protein were examined for reactivity with the serum pool from patients with CSD as well as individual serum samples from patients with CSD and controls. These sera had previously been subjected to IFA to determine the endpoint titer.

H. Identification and Characterization of Immunoreactive Clones

Approximately $1.2 \times 10^6$ recombinant phage clones were obtained. The quality of the resulting library was previously examined by assaying for cloning efficiency of a marker gene (3). For the purpose of that report, the 16S rRNA gene was chosen and was shown to hybridize with 0.125% of the clones. These results approach those predicted for random cloning and suggests that all DNA fragments should be represented in the *R. henselae* library. Approximately 0.2–0.3% of the 300,000 *R. henselae* recombinant plaques that were screened with the pool of sera from patients diagnosed with CSD, were immunoreactive. Ten of these immunoreactive recombinants were selected for further study and isolated by three or four rounds of plaque-purification. All ten were subcloned as pBluescript-based phagemids and were used to infect *E. coli* strain SOLR (Stratagene, Torrey Pines, Calif.). Each of the ten subclones appear to direct the synthesis of the same 17-kDa antigen that is highly reactive on immunoblots with the pool of sera from patients with CSD. A control strain of *E. coli* XL-1 harboring only the plasmid vector pBluescript SK, did not express the same immunoreactive 17-kDa antigen. *R. henselae* organisms when grown on blood agar appeared to express the 17-kDa antigen weakly, although expression of this antigen by *R. henselae* co-cultivated on Vero cells was not discernable. *R. quintana* also expressed the 17-kDa antigen that reacted with the pooled sera from CSD patients, suggesting that this antigen (or portions thereof) may be shared between *R. henselae* and *R. quintana*. The 17-kDa antigen expressed by *R. henselae* and the *E. coli* clones did not react with a control human serum pool from patients with no history of CSD. The antibody response from the serum pool did not appear to be directed to variety of different *R. henselae* antigens. Major immunoreactive antigens with approximate molecular masses of 14-, 68-, and 84-kDa are seen with *R. henselae* in addition to minor bands seen at 17-, 32-, and 48-kDa. The 17-kDa antigen expressed in *E. coli* appears to react with the serum pool much stronger than the protein as expressed in *R. henselae*. These results imply that the 17-kDa antigen is highly immunoreactive but not expressed at high levels in *R. henselae*.

I. Analysis of the Gene Encoding the 17-kDa Antigen

To determine if cloning bias was an explanation as to why clones expressing the 17-kDa antigen were isolated at such frequency, restriction endonuclease analysis was performed. Digestion of the plasmids from all ten recombinants expressing the 17-kDa antigen with EcoRI revealed seven different profiles. Thus, even though 17-kDa antigen-expressing clones represent the first ten clones isolated, at least seven different DNA fragments contain the entire gene. These results indicate that cloning bias is not responsible for isolating the same antigen-expressing clone by over-representation of a particular fragment of DNA in the library. Accordingly, these results taken together with the results showing few immunoreactive bands for *R. henselae* suggest that the 17-kDa antigen might be one of a few immunodominant antigens recognized by patients with CSD.

The gene for the 17-kDa antigen reactive with the pool of sera from patients with CSD has been localized within a 2.2 kilobase EcoRI fragment and the entire fragment has been sequenced. The gene coding for the 17-kDa antigen was localized to a single open reading frame by subcloning and immunoblot analysis with the serum pool from patients with CSD. This gene only directed synthesis of the 17-kDa antigen in *E. coli* when subcloned into pUC19 in the direction of the lacZ alpha peptide. Thus, a *R. henselae* promoter is either absent upstream of this gene or non-functional in *E. coli*. The open reading frame either consisted of 160 or 148 amino acids depending on which of the two putative initiator methionines that were identified are functional. The first potential initiator methionine is preceded by a polypurine rich sequence which is similar to the consensus ribosome binding site in *E. coli* (40). The second potential initiator methionine is preceded eight bases by a sequence identical to the consensus *E. coli* ribosome binding site. Assuming the second potential initiator methionine is used for the start of translation, then a deduced protein with 148 amino acids and a predicted molecular weight of 16,893 daltons is obtained. This is closer to the apparent molecular size of 17-kDa that is observed on immunoblots than that which would be predicted (18,245 daltons) if the first potential initiator methionine was used. The deduced amino acid sequence for the 17-kDa antigen gene does not share significant homology with any other bacterial protein in the GenBank database. Assuming the second potential initiator methionine is used, the deduced amino acid sequence shares several similarities to bacterial membrane-associated proteins. The first 18 amino acids are hydrophobic in nature and contain two lysine residues at the immediate amino-terminus (residues two and three). This type of motif is typical of bacterial outer surface proteins where the lysines residues interact with the phospholipids of the membrane and the following hydrophobic residues form a membrane-spanning or membrane anchor sequence (43). An amino acid sequence identical to the *E. coli* consensus signal peptidase cleavage site (A-X-A) is present at residues 18–20 after the second putative initiator codon. It is not known if this site is cleaved by *R. henselae* signal peptidases to yield a mature form of the 17-kDa antigen. The remaining 130 amino acid residues deduced from the 17-kDa antigen gene sequence are predominantly hydrophilic or neutral, with no long hydrophobic domains.

Regardless of which of the two potential initiator methionines are used for the start of translation, there is a short overlap with another long open reading frame. The reading frame shown upstream of the 17-kDa antigen gene continues at least an additional 380 nucleotides upstream of what is shown. The entire sequence of this open reading frame has not yet been obtained. It is likely that the 17-kDa antigen gene is part of an operon that is transcribed from a promoter upstream of this unidentified open reading frame. Likewise, a second unidentified open reading frame overlaps the 3' end of the 17-kDa antigen gene and continues at least for an additional 700 nucleotides. No sequences that are capable of forming stable loop and stem type secondary structures that are characteristic of bacterial transcription terminators are seen immediately downstream of the 17-kDa antigen gene. This third open reading frame may be a gene that is co-transcribed from a single promoter along with the 17-kDa antigen gene and the potential gene upstream of it. There are no regions upstream of the 17-kDa antigen gene with the correct spacing and homology to the *E. coli* consensus -35 (TTGACA) and -10 (TATAAT) promoter sequences (41). Although, Rochalimaea promoter sequences may differ from those of *E. coli*. The lack of potential promoter sequences and the expression of the 17-kDa antigen only when cloned in the direction of the vector lacZ promoter, provides further data that this gene is co-transcribed with an upstream gene.

J. Gene Fusion Construction

To create a highly-expressed hybrid fusion protein, the portion of the gene coding for amino acid residues 2–148 were synthesized by PCR amplification using the primers set forth in the Sequence Listing as SEQ ID NO:12 and SEQ ID NO:13. PCR primers were selected that permit in-frame fusion of the entire protein (assuming the second methionine is the start of translation) minus the methionine residue of this gene to the 13-kDa biotinylation tag sequence of expression vector PinPoint Xa-2. This results in a fusion protein which consists of the tag sequence (amino terminal portion) fused to the antigen (carboxy terminal portion) under the control of the lacZ promoter of vector pXa-2. The 30-kDa fusion protein is expressed efficiently in *E. coli* as determined by immunoblot analysis with streptavidin conjugated to horseradish peroxidase. A control consisting of an 8-kDa portion of an unrelated gene fused to the pXa-2 vector in *E. coli* strain XL-1 MRF' expresses a biotinylated protein of approximately 21-kDa. A naturally occurring biotinylated protein that has an apparent molecular mass of approximately 26-kDa is found in all three clones. This naturally occurring biotinylated protein has been observed in all K-12 strains of *E. coli* used for recombinant DNA purposes by the vector manufacturer (Promega Corp., Madison, Wisc.).

K. Immunoreactivity of the fusion protein

To examine the reactivity of the 30-kDa fusion protein with individual serum samples from patients with CSD as well as controls, immunoblot analysis was performed. When individual serum samples were reacted with the proteins expressed by the clone containing the fusion protein, 12 of 13 serum samples that were positive for antibody to Rochalimaea by the IFA assay were also reactive with the 30-kDa recombinant fusion protein. Likewise, 8 of 9 serum samples that were negative by IFA did not react by immunoblot with the 30-kDa fusion protein. When the immunoblot strips are examined only for reactivity of the 30-kDa fusion protein there is good correlation with clinical diagnosis of CSD and IFA titer. These results also indicate that a dominant epitope of the 17-kDa antigen recognized by serum from patients with CSD is retained in the fusion protein.

Throughout this application various publications are referenced by numbers within parentheses. Full citations for these publications are as follows. The disclosures of these publications in their entireties are hereby incorporated by reference into this application in order to more fully describe the state of the art to which this invention pertains.

REFERENCES 1. (Arnon, R. (Ed.) *Synthetic Vaccines* I:83–92, CRC Press, Inc., Boca Raton, Fla., 1987)
2. (Arnon, R. (Ed.) *Synthetic Vaccines* I:93–103, CRC Press, Inc., Boca Raton, Fla., 1987)
3. Anderson, B. E., J. E. Dawson, D. C. Jones, and K. H. Wilson. 1991. *Ehrlichia chaffeensis*, a new species associated with human ehrlichiosis. *J. Clin. Microbiol.* 29:2838–2842.
4. Anderson, B., C. Kelly, R. Threlkel, and K. Edwards. 1993. Detection of *Rochalimaea henselae* in cat-scratch disease skin test antigens. *J. Infect. Dis.* 168:1034–1036.
5. Anderson, B., and G. McDonald. 1993. Construction of DNA libraries of A-T rich organisms using EcoRI star activity. *Anal. Biochem.* 211:325–327.
6. Anderson, B., K. Sims, D. Jones, W. Dewitt, and W. Bibb. 1993. Molecular cloning of *Rochalimaea henselae* antigens. D-90, p. 111. Program Abstr. 93rd Annu. Meet. Am. Soc. Microbiol., 1993, Washington D.C.
7. Brenner D. J., D. G. Hollis, C. W. Moss, C. K. English, G. S. Hall, J. V. Vincent, J. Radosevic, K. A. Birkness, W. F. Bibb, F. D. Quinn, B. Swaminathan, R. E. Weaver, M. W. Reeves, S. P. O'Connor, P. S. Hayes, F. C. Tenover, A. G. Steigerwalt, B. A. Perkins, M. I. Daneshvar, B. C. Hill, J. A. Washington, T. C. Woods, S. B. Hunter, T. L. Hadfield, G. W. Ajello, A. F. Kaufmann, D. J. Wear, and J. D. Wenger. 1991. Proposal of Afipia, gen. nov., with *Afipia felis* sp. nov. (formerly the cat scratch disease bacillus), *Afipia clevelandensis* sp. nov. (formerly the Clevland Clinic Foundation strain), *Afipia broomeae* sp. nov., and three unnamed genospecies. *J. Clin. Microbiol.* 29:2450–2460.
8. Daly, J. S., M. G. Worthington, D. J. Brenner, C. W. Moss, D. G. Hollis, R. S. Weyant, A. G. Steigerwalt, R. E. Weaver, M. I. Daneshvar, and S. P. O'Connor. 1993. *Rochalimaea elizabethae* sp. nov. isolated from a patient with endocarditis. *J. Clin. Microbiol.* 31:872–881.
9. Dolan, M. J., M. T. Wong, R. L. Regnery, J. H. Jorgensen, M. Garcia, J. Peters, and D. Drehner. 1993. Syndrome of *Rochalimaea henselae* suggesting cat scratch disease. *Ann. Intern. Med.* 118:331–336.
10. Drancourt, M., and D. Raoult. 1992. Abstr. Tenth sesquiannual meeting of the American Society for Rickettsiology and Rickettsial Diseases, Hamilton, Mont.
11. English, C. K., D. J. Wear, A. M. Margileth, C. R. Lissner, and G. P. Walsh. 1988. Cat-scratch disease: isolation and culture of the bacterial agent. *JAMA* 259:1347–1352.
12. Erler, B. S., A. M. Jiminez, M. L. Gedebou, J. W. Said, and W. S. Nichols. 1993. Absence of *Rochalimaea henselae* sequences in cat scratch disease lymph nodes using a polymerase chain reaction assay. *Modern Pathology* 6:105A, abstract 605.
13. Gerber, M. A., P. Rapacz, S. S. Kalter, and M. Ballow. 1986. Cell-mediated immunity in cat-scratch disease. *J. Allergy Clin. Immunol.* 78:887–890.
14. Harlow and Lane, Harlow and Lane, *Antibodies: A Laboratory Manual*, Cold Spring Harbor Laboratory, Cold Spring Harbor, N.Y., 1988.
15. Koehler, J. E., F. D. Quinn, T. G. Berger, P. E. LeBoit, and J. W. Tappero. 1992. Isolation of Rochalimaea species from cutaneous and osseous lesions of bacillary angiomatosis. *N. Engl. J. Med.* 327:1625–1631.
16. Lennette et al., *Manual of Clinical Microbiology*, 14th Ed., Amer. Soc. for Microbiology, Washington, D.C., 1985)
17. Lipinska, B., S. Sharma, and C. Georgopoulos. 1988. Sequence analysis and regulation of the htrA gene of *Escherichia coli*: a $^{32}$-independent mechanism of heat-inducible transcription. *Nucleic Acids Res.* 16:10053–10067.
18. Lucey, D., M. J. Dolan, C. W. Moss, M. Garcia, D. G. Hollis, S. Wenger, G. Morgan, R. Almeida, D. Leong, K. S. Greisen, D. F. Welch, and L. N. Slater. 1992. Relapsing illness due to *Rochalimaea henselae* in immunocompetent hosts: implication for therapy and new epidemiological associations. *Clin. Infect. Dis.* 14:683–688.
19. Margileth, A. M. 1992. Antibiotic therapy for cat-scratch disease: clinical study of therapeutic outcome in 268 patients and a review of the literature. *Pediatr. Infect. Dis.* 11:474–478.
20. Maniatis et al. *Molecular Cloning: A Laboratory Manual*, Cold Spring Harbor, N.Y., 1982)
21. Patnaik, M., W. A. Schwartzman, N. E. Barka, and J. B. Peter. 1992. Letter. *Lancet* 340:971.
22. O'Connor, S. P., M. Dorsch, A. G. Steigerwalt, D. J. Brenner, and E. Stackebrandt. 1991. 16S rRNA sequences of *Bartonella bacilliformis* and cat scratch disease bacillus reveal phylogenetic relationships with the alpha-2 subgroup of the class Proteobacteria. *J. Clin. Microbiol.* 29:2144–2150.
23. Regnery, R. L., B. E. Anderson, J. E. Clarridge, M. C. Rodriquez-Barradas, D. C. Jones, and J. H. Carr. 1992. Characterization of a novel Rochalimaea species, *R. henselae* sp. nov., isolated from blood of a febrile human immunodeficiency virus-positive patient. *J. Clin. Microbiol.* 30:265–274.
24. Regnery, R. L., J. G. Olson, B. A. Perkins, and W. Bibb. 1992. Serological response to "*Rochalimaea henselae*" antigen in suspected cat-scratch disease. *Lancet* 339:1443–1445.
25. Regnery et al., *J. Bacteriol.* 173:1576–1589, 1991
26. Wilson et al., *J. Clin. Microbiol.* 28:1942–1946, 1990
27. Relman, D. A., P. W. Lepp, K. N. Sadler, and T. M. Schmidt. 1992. Phylogenetic relationships among the agent of bacillary angiomatosis, *Bartonella bacilliformis*, and other alpha-proteobacteria. *Mol. Microbiol.* 6:1801–1807.
28. Relman D. A., J. S. Loutit, T. M. Schmidt, S. Falkow, and L. S. Tompkins. 1990. The agent of bacillary angiomatosis. *N. Engl. J. Med.* 323:1573–1580.
29. Sambrook et al., *Molecular Cloning: A Laborabory Manual*, 2nd Ed., Cold Spring Harbor Laboratory, Cold Spring Harbor, N.Y., 1989)
30. Slater, L. N., D. F. Welch, D. Hensel, and D. W. Coody. 1990. A newly recognized fastidious gram-negative pathogen as a cause of fever and bacteremia. *N. Engl. J. Med.* 323:1587–1593.
31. Tappero, J. W., J. Mohle-Boetani, J. E. Koehler, B. Swaminathan, T. G. Berger, P. E. LeBoit, L. L. Smith, J. D. Wenger, R. W. Pinner, C. A. Kemper, and A. L. Reingold. 1993. The epidemiology of bacillary angiomatosis and bacillary peliosis. *JAMA* 269:770–775.
32. Upholt *Nucleic Acids Res.* 4:1257–1265, 1977
33. Welch, D. F., D. M. Hensel, D. A. Pickett, V. H. San Joaquin, A. Robinson, and L. N. Slater. 1993. Bacteremia due to *Rochalimaea henselae* in a child: practical identification of isolates in the clinical laboratory. *J. Clin. Microbiol.* 31:2381–2386.
34. Welch, D. F., D. A. Pickett, L. N. Slater, A. G. Steigerwalt, and D. J. Brenner. 1992. *Rochalimaea henselae* sp. nov., a cause of septicemia, bacillary angiomatosis, and parenchymal bacillary peliosis. *J. Clin. Microbiol.* 30:275–280.

35. Weisberg et al. *Science* 230:556–558, 1985
36. Wu, D. Y., L. Ugozzoli, B. K. Pal, and R. B. Wallace. 1989. Allele-specific enzymatic amplification of -globin genomic DNA for diagnosis of sickle cell anemia. *Proc. Natl. Acad. Sci. USA* 86:2757–2760.
37. Zangwill, K. M., D. H. Hamilton, B. A. Perkins, R. L. Regnery, B. D. Plikaytis, J. L. Hadler, M. L. Cartter, and J. D. Wenger. 1993. Cat scratch disease in Connecticut. *N. Engl. J. Med.* 329:8–13.
38. Ferretti et al. *Proc. Natl. Acad. Sci.* 82:599–603, 1986
39. Wosnick et al. *Gene* 76:153–160, 1989
40. Gold, L., D. Pribnow, T. Schneider, S. Shinedling, B. Singer, and G. Stormo. 1981. Translation initiation in prokatyotes. Ann. Rev. Microbiol. 35:365–407.
41. Hawley, D. K. and W. R. McClure. 1983. Compilation and analysis of *Escherichia coli* promoter DNA sequences. *Nuc. Acids Res.* 11:2237–2255.
42. Mui, B. S. K., M. E. Mulligan, and W. L. George. 1990. Response of HIV-associated disseminated cat-scratch disease to treatment with doxycycline. Am J. Med. 89:229–231.
43. Silhavy, T. J., S. A. Benson, and S. D. Emr. 1983. Mechanisms of protein localization. Microbiol. Rev. 47:313–344.
44. Zhang, H., R. Scholl, J. Browse, and C. Somerville. 1988. Double stranded DNA as a choice for DNA sequencing. Nuc. Acids Res. 16:1220.

---

What is claimed is:

1. A method of diagnosing current or previous cat scratch disease in a subject by detecting the presence of an antibody that specifically binds Rochalimaea henselae, wherein the detecting step comprises the steps of contacting an antibody-containing fluid or tissue sample from the subject with an amount of the purified polypeptide set forth in the Sequence Listing as SEQ ID NO:11 or an immunogenic fragment thereof which binds to the antibody, detecting the binding of the purified polypeptide or immunogenic fragment thereof to the antibody, and correlating the presence of an antibody that specifically binds to the purified polypeptide or immunogenic fragment thereof with cat scratch disease in the subject.

2. A method of diagnosing current or previous cat scratch disease in a subject by detecting the presence of an antibody that specifically binds Rochalimaea henselae, wherein the detecting step comprises the steps of contacting an antibody-containing fluid or tissue sample from the subject with an amount of an immunogenic polypeptide encoded by a nucleic acid which can specifically hybridize with the nucleic acid encoding the amino acid sequence set forth in the Sequence Listing as SEQ ID NO:11 under the stringency conditions of 60° C. and 5× SSC, followed by the initial washing condition of room temperature, 2× SSC and 0.1% SDS, and two secondary washes with stringency conditions of 50° C., 0.5% SSC and 0.1% SDS.

3. A method of diagnosing bacillary angiomatosis in a subject by detecting the presence of an antibody that specifically binds *Rochalimaea henselae*, wherein the detecting step comprises the steps of contacting an antibody-containing fluid or tissue sample from the subject with an amount of the purified polypeptide set forth in the Sequence Listing as SEQ ID NO:11 or immunogenic fragment thereof which binds to the antibody, and detecting the binding of the purified polypeptide or immunogenic fragment thereof to the antibody.

4. A diagnostic kit for detecting the presence of a serum antibody specifically reactive with *Rochalimaea henselae* or an immunogenic fragment thereof comprising: the purified polypeptide set forth in the Sequence Listing as SEQ ID NO:11 or immunogenic fragment thereof bound to a substrate; a secondary antibody reactive with the serum antibody specifically reactive with the purified polypeptide or an immunogenic fragment thereof; and a reagent for detecting a reaction of the secondary antibody with the serum antibody.

5. A method of diagnosing current or previous cat scratch disease in a subject by detecting the presence of an antibody that specifically binds *Rochalimea henselae*, wherein the detecting step comprises the steps of contacting an antibody-containing fluid or tissue sample from the subject with an amount of the purified polypeptide set forth in the Sequence Listing as SEQ ID NO:7 or an immunogenic fragment thereof which binds to the antibody, detecting the binding of the purified polypeptide or immunogenic fragment thereof to the antibody, and correlating the presence of an antibody that specifically binds to the polypeptide or immunogenic fragment thereof with cat scratch disease in the subject.

6. A method of diagnosing current or previous cat scratch disease in a subject by detecting the presence of an antibody that specifically binds *Rochalimaea henselae*, wherein the detecting step comprises the steps of contacting an antibody-containing fluid or tissue sample from the subject with an amount of an immunogenic polypeptide encoded by a nucleic acid which can specifically hybridize with the nucleic acid encoding the amino acid sequence set forth in the Sequence Listing as SEQ ID NO:7 under stringency conditions of 60° C. and 5× SSC, followed by an initial wash with stringency conditions of room temperature, 2× SSC and 0.1% SDS, and two secondary washes with stringency conditions of 50° C., 0.5% SSC and 0.1% SDS.

7. A method of diagnosing current or previous cat scratch disease in a subject by detecting the presence of an antibody that specifically binds *Rochalimea henselae*, wherein the detecting step comprises the steps of contacting an antibody-containing fluid or tissue sample from the subject with an amount of the 30-kDa fusion protein produced by subcloning the *Rochalimea henselae* polypeptide set forth in the Sequence Listing as SEQ ID NO:11 as a biotinylated fusion protein in the expression vector PinPoint Xa-2, detecting the binding of the 30-kDa fusion protein to the antibody, and correlating the presence of an antibody that specifically binds to the 30-kDa fusion protein with cat scratch disease in the subject.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GATTCAATTG GTTGAAGGA GGCT                                                      2 4

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GATTCAATTG GTTGAAAGA GGCT                                                      2 4

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TCACATCACC AGGACGTATT C                                                          2 1

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

TCACATCACC AGGGCGTATT C									21

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GGTGCGTTAA TTACCGATCC									20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GGCGCTTTGA TTACTGATCC									20

( 2 ) INFORMATION FOR SEQ ID NO:7:

( i ) SEQUENCE CHARACTERISTICS:
        ( A ) LENGTH: 1791 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 141..1652

( x i ) SEQUENCE DESCRIPTION: SEQ ID NO:7:

```
GAAGAGCAAT AAAAAGAAAA AAGAATGGTT TTTTAGTGAT TTTTTAGTA CTCCAATTTA        60

GACAGAAAAC GGTAAGGTTT GTTATTTTAT AAAGGACTGC AATTGGGATA ACAATATGAT      120

TAAATAGGAG CACATACCAA ATG GTT AAA AAA ACT TTC TTC ACA ACA TTA         170
                     Met Val Lys Lys Thr Phe Phe Thr Thr Leu
                      1               5                  10

GCC GCA GTA AGT TTT TCT GCT GCT TTA GAA ACT GCA CTG TTT TTT AGT       218
Ala Ala Val Ser Phe Ser Ala Ala Leu Glu Thr Ala Leu Phe Phe Ser
                 15                  20                  25

GGA TGT GGA TCA AGC TTG TGG ACG ACA AAA GCT CAT GCA AAT TCT GTA       266
Gly Cys Gly Ser Ser Leu Trp Thr Thr Lys Ala His Ala Asn Ser Val
         30                  35                  40

TTT AGT TCA TTA ATG CAA CAG CAG GGA TTT GCA GAT ATT GTT TCT CAA       314
Phe Ser Ser Leu Met Gln Gln Gln Gly Phe Ala Asp Ile Val Ser Gln
             45                  50                  55

GTA AAG CCT GCT GTT GTT TCA GTG CAG GTG AAG AGC AAT AAA AAG AAA       362
Val Lys Pro Ala Val Val Ser Val Gln Val Lys Ser Asn Lys Lys Lys
     60                  65                  70

AAA GAA TGG TTT TTT AGT GAT TTT TTT AGT ACT CCG GGT TTT GAC CAA       410
Lys Glu Trp Phe Phe Ser Asp Phe Phe Ser Thr Pro Gly Phe Asp Gln
 75                  80                  85                  90
```

-continued

| | | | | | | | | | | | | | | | | |
|---|---|---|---|---|---|---|---|---|---|---|---|---|---|---|---|---|
| TTA | CCA | GAT | CAA | CAT | CCC | TTG | AAA | AAG | TTT | TTT | CAA | GAT | TTT | TAT | AAT | 458 |
| Leu | Pro | Asp | Gln | His 95 | Pro | Leu | Lys | Lys 100 | Phe | Phe | Gln | Asp | Phe | Tyr 105 | Asn | |
| CGT | GAT | AAG | CCT | AGT | AAT | AAA | TCT | TTG | CAA | CGT | TCG | CAT | AGA | CTG | CGT | 506 |
| Arg | Asp | Lys | Pro 110 | Ser | Asn | Lys | Ser | Leu 115 | Gln | Arg | Ser | His | Arg 120 | Leu | Arg | |
| CCT | ATA | GCT | TTT | GGA | TCG | GGT | TTT | TTT | ATC | TCG | TCT | GAT | GGT | TAT | ATT | 554 |
| Pro | Ile | Ala 125 | Phe | Gly | Ser | Gly | Phe | Phe 130 | Ile | Ser | Ser | Asp 135 | Gly | Tyr | Ile | |
| GTG | ACC | AAT | AAT | CAT | GTG | ATT | TCT | GAT | GGC | ACA | AGT | TAC | GCT | GTT | GTT | 602 |
| Val | Thr | Asn 140 | Asn | His | Val | Ile 145 | Ser | Asp | Gly | Thr | Ser 150 | Tyr | Ala | Val | Val | |
| CTT | GAT | GAC | GGT | ACA | GAA | CTG | AAT | GCA | AAA | CTC | ATT | GGA | ACG | GAC | CCA | 650 |
| Leu 155 | Asp | Asp | Gly | Thr | Glu 160 | Leu | Asn | Ala | Lys | Leu 165 | Ile | Gly | Thr | Asp | Pro 170 | |
| CGA | ACT | GAT | CTT | GCA | GTA | TTA | AAA | GTC | AAT | GAA | AAA | AGA | AAA | TTT | TCG | 698 |
| Arg | Thr | Asp | Leu | Ala 175 | Val | Leu | Lys | Val | Asn 180 | Glu | Lys | Arg | Lys | Phe 185 | Ser | |
| TAC | GTT | GAT | TTT | GGT | GAT | GAT | TCA | AAA | CTT | CGT | GTT | GGT | GAT | TGG | GTT | 746 |
| Tyr | Val | Asp | Phe 190 | Gly | Asp | Asp | Ser | Lys 195 | Leu | Arg | Val | Gly | Asp 200 | Trp | Val | |
| GTT | GCT | ATT | GGT | AAT | CCA | TTT | GGT | CTT | GGT | GGA | ACT | GTG | ACA | GCA | GGT | 794 |
| Val | Ala | Ile 205 | Gly | Asn | Pro | Phe | Gly 210 | Leu | Gly | Gly | Thr | Val 215 | Thr | Ala | Gly | |
| ATC | GTT | TCA | GCA | CGT | GGA | CGT | GAT | ATC | GGT | ACC | GGT | GTT | TAT | GAT | GAT | 842 |
| Ile | Val | Ser 220 | Ala | Arg | Gly | Arg 225 | Asp | Ile | Gly | Thr | Gly 230 | Val | Tyr | Asp | Asp | |
| TTT | ATT | CAG | ATT | GAT | GCT | GCA | GTT | AAT | CGA | GGA | AAT | TCT | GGA | GGT | CCA | 890 |
| Phe 235 | Ile | Gln | Ile | Asp | Ala 240 | Ala | Val | Asn | Arg | Gly 245 | Asn | Ser | Gly | Gly | Pro 250 | |
| ACT | TTT | GAT | CTT | AAC | GGA | AAG | GTT | GTT | GGA | GTG | AAT | ACG | GCA | ATT | TTT | 938 |
| Thr | Phe | Asp | Leu | Asn 255 | Gly | Lys | Val | Val | Gly 260 | Val | Asn | Thr | Ala | Ile 265 | Phe | |
| TCT | CCT | TCT | GGG | GGC | AAC | GTT | GGG | ATT | GCT | TTC | GCT | ATT | CCG | GCA | GCA | 986 |
| Ser | Pro | Ser | Gly 270 | Gly | Asn | Val | Gly | Ile 275 | Ala | Phe | Ala | Ile | Pro 280 | Ala | Ala | |
| ACA | GCG | AAC | GAG | GTT | GTG | CAA | CAA | CTT | ATC | GAA | AAA | GGT | TTA | GTT | CAG | 1034 |
| Thr | Ala | Asn 285 | Glu | Val | Val | Gln | Gln 290 | Leu | Ile | Glu | Lys | Gly 295 | Leu | Val | Gln | |
| CGT | GGT | TGG | CTT | GGG | GTT | CAG | ATT | CAG | CCT | GTA | ACA | AAA | GAA | ATT | TCT | 1082 |
| Arg | Gly 300 | Trp | Leu | Gly | Val | Gln 305 | Ile | Gln | Pro | Val | Thr 310 | Lys | Glu | Ile | Ser | |
| GAT | TCA | ATT | GGT | TTG | AAG | GAG | GCT | AAA | GGT | GCG | TTA | ATT | ACC | GAT | CCA | 1130 |
| Asp 315 | Ser | Ile | Gly | Leu | Lys 320 | Glu | Ala | Lys | Gly | Ala 325 | Leu | Ile | Thr | Asp | Pro 330 | |
| TTA | AAG | GGG | CCA | GCC | GCA | AAA | GCT | GGT | ATC | AAG | GCA | GGT | GAT | GTT | ATT | 1178 |
| Leu | Lys | Gly | Pro | Ala 335 | Ala | Lys | Ala | Gly | Ile 340 | Lys | Ala | Gly | Asp | Val 345 | Ile | |
| ATT | TCG | GTA | AAT | GGT | GAG | AAG | ATT | AAT | GAT | GTC | CGT | GAT | CTA | GCA | AAG | 1226 |
| Ile | Ser | Val | Asn 350 | Gly | Glu | Lys | Ile | Asn 355 | Asp | Val | Arg | Asp | Leu 360 | Ala | Lys | |
| CGT | ATT | GCA | AAT | ATG | AGC | CCA | GGA | GAA | ACA | GTA | ACC | TTA | GGA | GTT | TGG | 1274 |
| Arg | Ile | Ala | Asn 365 | Met | Ser | Pro | Gly | Glu 370 | Thr | Val | Thr | Leu | Gly 375 | Val | Trp | |
| AAA | TCT | GGT | AAA | GAA | GAG | AAT | ATT | AAG | GTT | AAA | CTT | GAT | TCG | ATG | CCT | 1322 |
| Lys | Ser | Gly 380 | Lys | Glu | Glu | Asn | Ile 385 | Lys | Val | Lys | Leu | Asp 390 | Ser | Met | Pro | |
| GAA | GAC | GAA | AAT | ATG | AAG | GAT | GGC | TCA | AAA | TAT | TCA | AAT | GAG | CAC | GGT | 1370 |
| Glu | Asp | Glu | Asn | Met 400 | Lys | Asp | Gly | Ser | Lys 405 | Tyr | Ser | Asn | Glu | His 410 | Gly | |

```
AAT  TCA  GAT  GAA  ACA  TTG  GAA  GAT  TAT  GGT  TTG  ATT  GTT  GCT  CCT  TCT           1418
Asn  Ser  Asp  Glu  Thr  Leu  Glu  Asp  Tyr  Gly  Leu  Ile  Val  Ala  Pro  Ser
               415                      420                           425

GAT  GAT  GGC  CTA  GGG  TTG  GTT  GTA  ACT  GAT  GTA  GAT  CCA  GAT  TCT  GAT           1466
Asp  Asp  Gly  Leu  Gly  Leu  Val  Val  Thr  Asp  Val  Asp  Pro  Asp  Ser  Asp
                    430                      435                440

GCT  GCA  GAT  AAA  GGA  ATA  CGT  CCT  GGT  GAT  GTG  ATT  GTA  ACA  GTT  AAT           1514
Ala  Ala  Asp  Lys  Gly  Ile  Arg  Pro  Gly  Asp  Val  Ile  Val  Thr  Val  Asn
               445                      450                      455

AAT  AAA  TCT  GTT  AAA  AAG  GTC  TCT  GAT  ATT  ACG  GAC  ACT  ATC  AAA  AAT           1562
Asn  Lys  Ser  Val  Lys  Lys  Val  Ser  Asp  Ile  Thr  Asp  Thr  Ile  Lys  Asn
          460                      465                      470

GCC  CAA  AAG  TTA  GGA  CGA  AAA  GCC  ATA  CTT  CTA  CAA  GTG  CGA  ACA  AAT           1610
Ala  Gln  Lys  Leu  Gly  Arg  Lys  Ala  Ile  Leu  Leu  Gln  Val  Arg  Thr  Asn
475                      480                      485                           490

GAT  CAA  AAT  CGT  TTT  GTC  GCT  CTT  CCT  ATT  TTT  AAA  AAA  TAATACTTGA              1659
Asp  Gln  Asn  Arg  Phe  Val  Ala  Leu  Pro  Ile  Phe  Lys  Lys
                    495                      500

TTAATGGTAG  GGCAGAAGTT  TTGTAAACTT  TTGTCCTACA  AACGTGATTT  GATAAAATAA                   1719

CGGAGATGCG  TTTTATGAAG  ATACTCGTTA  TCGAAGATGA  TCATGAAACG  GGACGTTATC                   1779

TCGAAAAGCT  TT                                                                            1791
```

( 2 ) INFORMATION FOR SEQ ID NO:8:

( i ) SEQUENCE CHARACTERISTICS:
        ( A ) LENGTH: 503 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met  Val  Lys  Lys  Thr  Phe  Phe  Thr  Thr  Leu  Ala  Ala  Val  Ser  Phe  Ser
 1             5                       10                      15

Ala  Ala  Leu  Glu  Thr  Ala  Leu  Phe  Phe  Ser  Gly  Cys  Gly  Ser  Ser  Leu
               20                      25                      30

Trp  Thr  Thr  Lys  Ala  His  Ala  Asn  Ser  Val  Phe  Ser  Ser  Leu  Met  Gln
          35                      40                      45

Gln  Gln  Gly  Phe  Ala  Asp  Ile  Val  Ser  Gln  Val  Lys  Pro  Ala  Val  Val
     50                      55                      60

Ser  Val  Gln  Val  Lys  Ser  Asn  Lys  Lys  Lys  Glu  Trp  Phe  Phe  Ser
 65                      70                      75                      80

Asp  Phe  Phe  Ser  Thr  Pro  Gly  Phe  Asp  Gln  Leu  Pro  Asp  Gln  His  Pro
                    85                      90                      95

Leu  Lys  Lys  Phe  Phe  Gln  Asp  Phe  Tyr  Asn  Arg  Asp  Lys  Pro  Ser  Asn
                    100                     105                     110

Lys  Ser  Leu  Gln  Arg  Ser  His  Arg  Leu  Arg  Pro  Ile  Ala  Phe  Gly  Ser
               115                     120                     125

Gly  Phe  Phe  Ile  Ser  Ser  Asp  Gly  Tyr  Ile  Val  Thr  Asn  Asn  His  Val
     130                     135                     140

Ile  Ser  Asp  Gly  Thr  Ser  Tyr  Ala  Val  Val  Leu  Asp  Asp  Gly  Thr  Glu
145                      150                     155                     160

Leu  Asn  Ala  Lys  Leu  Ile  Gly  Thr  Asp  Pro  Arg  Thr  Asp  Leu  Ala  Val
                    165                     170                     175

Leu  Lys  Val  Asn  Glu  Lys  Arg  Lys  Phe  Ser  Tyr  Val  Asp  Phe  Gly  Asp
                    180                     185                     190

Asp  Ser  Lys  Leu  Arg  Val  Gly  Asp  Trp  Val  Val  Ala  Ile  Gly  Asn  Pro
               195                     200                     205
```

| Phe | Gly | Leu | Gly | Gly | Thr | Val | Thr | Ala | Gly | Ile | Val | Ser | Ala | Arg | Gly |
|---|---|---|---|---|---|---|---|---|---|---|---|---|---|---|---|
| | 210 | | | | 215 | | | | | 220 | | | | | |

| Arg | Asp | Ile | Gly | Thr | Gly | Val | Tyr | Asp | Asp | Phe | Ile | Gln | Ile | Asp | Ala |
|---|---|---|---|---|---|---|---|---|---|---|---|---|---|---|---|
| 225 | | | | | 230 | | | | | 235 | | | | | 240 |

| Ala | Val | Asn | Arg | Gly | Asn | Ser | Gly | Gly | Pro | Thr | Phe | Asp | Leu | Asn | Gly |
|---|---|---|---|---|---|---|---|---|---|---|---|---|---|---|---|
| | | | | 245 | | | | | 250 | | | | | 255 | |

| Lys | Val | Val | Gly | Val | Asn | Thr | Ala | Ile | Phe | Ser | Pro | Ser | Gly | Gly | Asn |
|---|---|---|---|---|---|---|---|---|---|---|---|---|---|---|---|
| | | | 260 | | | | | 265 | | | | | 270 | | |

| Val | Gly | Ile | Ala | Phe | Ala | Ile | Pro | Ala | Ala | Thr | Ala | Asn | Glu | Val | Val |
|---|---|---|---|---|---|---|---|---|---|---|---|---|---|---|---|
| | | 275 | | | | | 280 | | | | | 285 | | | |

| Gln | Gln | Leu | Ile | Glu | Lys | Gly | Leu | Val | Gln | Arg | Gly | Trp | Leu | Gly | Val |
|---|---|---|---|---|---|---|---|---|---|---|---|---|---|---|---|
| | 290 | | | | | 295 | | | | | 300 | | | | |

| Gln | Ile | Gln | Pro | Val | Thr | Lys | Glu | Ile | Ser | Asp | Ser | Ile | Gly | Leu | Lys |
|---|---|---|---|---|---|---|---|---|---|---|---|---|---|---|---|
| 305 | | | | | 310 | | | | | 315 | | | | | 320 |

| Glu | Ala | Lys | Gly | Ala | Leu | Ile | Thr | Asp | Pro | Leu | Lys | Gly | Pro | Ala | Ala |
|---|---|---|---|---|---|---|---|---|---|---|---|---|---|---|---|
| | | | | 325 | | | | | 330 | | | | | 335 | |

| Lys | Ala | Gly | Ile | Lys | Ala | Gly | Asp | Val | Ile | Ile | Ser | Val | Asn | Gly | Glu |
|---|---|---|---|---|---|---|---|---|---|---|---|---|---|---|---|
| | | | 340 | | | | | 345 | | | | | 350 | | |

| Lys | Ile | Asn | Asp | Val | Arg | Asp | Leu | Ala | Lys | Arg | Ile | Ala | Asn | Met | Ser |
|---|---|---|---|---|---|---|---|---|---|---|---|---|---|---|---|
| | | 355 | | | | | 360 | | | | | 365 | | | |

| Pro | Gly | Glu | Thr | Val | Thr | Leu | Gly | Val | Trp | Lys | Ser | Gly | Lys | Glu | Glu |
|---|---|---|---|---|---|---|---|---|---|---|---|---|---|---|---|
| | 370 | | | | | 375 | | | | | 380 | | | | |

| Asn | Ile | Lys | Val | Lys | Leu | Asp | Ser | Met | Pro | Glu | Asp | Glu | Asn | Met | Lys |
|---|---|---|---|---|---|---|---|---|---|---|---|---|---|---|---|
| 385 | | | | | 390 | | | | | 395 | | | | | 400 |

| Asp | Gly | Ser | Lys | Tyr | Ser | Asn | Glu | His | Gly | Asn | Ser | Asp | Glu | Thr | Leu |
|---|---|---|---|---|---|---|---|---|---|---|---|---|---|---|---|
| | | | | 405 | | | | | 410 | | | | | 415 | |

| Glu | Asp | Tyr | Gly | Leu | Ile | Val | Ala | Pro | Ser | Asp | Asp | Gly | Leu | Gly | Leu |
|---|---|---|---|---|---|---|---|---|---|---|---|---|---|---|---|
| | | | 420 | | | | | 425 | | | | | 430 | | |

| Val | Val | Thr | Asp | Val | Asp | Pro | Asp | Ser | Asp | Ala | Ala | Asp | Lys | Gly | Ile |
|---|---|---|---|---|---|---|---|---|---|---|---|---|---|---|---|
| | | 435 | | | | | 440 | | | | | 445 | | | |

| Arg | Pro | Gly | Asp | Val | Ile | Val | Thr | Val | Asn | Asn | Lys | Ser | Val | Lys | Lys |
|---|---|---|---|---|---|---|---|---|---|---|---|---|---|---|---|
| | 450 | | | | | 455 | | | | | 460 | | | | |

| Val | Ser | Asp | Ile | Thr | Asp | Thr | Ile | Lys | Asn | Ala | Gln | Lys | Leu | Gly | Arg |
|---|---|---|---|---|---|---|---|---|---|---|---|---|---|---|---|
| 465 | | | | | 470 | | | | | 475 | | | | | 480 |

| Lys | Ala | Ile | Leu | Leu | Gln | Val | Arg | Thr | Asn | Asp | Gln | Asn | Arg | Phe | Val |
|---|---|---|---|---|---|---|---|---|---|---|---|---|---|---|---|
| | | | | 485 | | | | | 490 | | | | | 495 | |

| Ala | Leu | Pro | Ile | Phe | Lys | Lys |
|---|---|---|---|---|---|---|
| | | | 500 | | | |

(2) INFORMATION FOR SEQ ID NO:9:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:9:

AATCTAGATT GCTTTCGCTA TTCCGGC     27

(2) INFORMATION FOR SEQ ID NO:10:

(i) SEQUENCE CHARACTERISTICS:
(A) LENGTH: 29 base pairs
(B) TYPE: nucleic acid
(C) STRANDEDNESS: single ( D ) TOPOLOGY: linear ( i i ) MOLECULE TYPE: DNA (genomic)

( x i ) SEQUENCE DESCRIPTION: SEQ ID NO:10:

AAGGATCCAT TTGTTCGCAC TTGTAGAAG    29

( 2 ) INFORMATION FOR SEQ ID NO:11:

( i ) SEQUENCE CHARACTERISTICS:
( A ) LENGTH: 660 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 123..605

( x i ) SEQUENCE DESCRIPTION: SEQ ID NO:11:

```
TCCGTTGTTG CAGAACTTAA CTTACGTGGA ATGAATGATG AGATCGCCGT CTTAAGCGGT    60

ACAACAAAGA ATATTGAACT GGTGAACCAA ATTATCAGCG AATATGGAGC AGACCCAGAC   120

AT ATG GCT GCC TAT ATT TCA TCA AAG GAG AGA AAA TCA ATG AAA AAA      167
   Met Ala Ala Tyr Ile Ser Ser Lys Glu Arg Lys Ser Met Lys Lys
   1               5                   10                  15

TAT AGC TTA GTC ACA TTG TTA TCT TTA TTT TGC ATC TCT CAT GCA AAA    215
Tyr Ser Leu Val Thr Leu Leu Ser Leu Phe Cys Ile Ser His Ala Lys
                20                  25                  30

GCA CAA ACA GCA ACC CTT ACT GAT GAA TAT TAT AAA AAA GCC TTA GAA    263
Ala Gln Thr Ala Thr Leu Thr Asp Glu Tyr Tyr Lys Lys Ala Leu Glu
            35                  40                  45

AAC ACG CAA AAA TTA GAC GTT GCA AAA TCA CAA ACA GCT GAG TCT ATT    311
Asn Thr Gln Lys Leu Asp Val Ala Lys Ser Gln Thr Ala Glu Ser Ile
        50                  55                  60

TAT GAA TCT GCA ACA CAA ACT GCA AAC AAA ATT AAG GAC ATA AAC AAT    359
Tyr Glu Ser Ala Thr Gln Thr Ala Asn Lys Ile Lys Asp Ile Asn Asn
    65                  70                  75

CAA CTT GCA AAT CTT AAA GCA GAT ACA AAG ACT AAA CCT GAA CAA TTG    407
Gln Leu Ala Asn Leu Lys Ala Asp Thr Lys Thr Lys Pro Glu Gln Leu
80                  85                  90                  95

CAA GCC CTG CAA ATA GAG CTG ACT CTT CTC CAG GCA CAG CTG CAA GCG    455
Gln Ala Leu Gln Ile Glu Leu Thr Leu Leu Gln Ala Gln Leu Gln Ala
                100                 105                 110

GAT ACT TTA AAA ATC CAG TCT CTT GCT ATG ATT CAA GCA AAA GAT ACG    503
Asp Thr Leu Lys Ile Gln Ser Leu Ala Met Ile Gln Ala Lys Asp Thr
            115                 120                 125

AAA ACA AAA GAA GAA TTG CGT GAA GAG CAA ACA CAA AAA AAG CAT GAA    551
Lys Thr Lys Glu Glu Leu Arg Glu Glu Gln Thr Gln Lys Lys His Glu
        130                 135                 140

GAT CTT CAA AAA CAA TTA AAA GAA AAA CTT GAG AAA TCT GAT GTC CGA    599
Asp Leu Gln Lys Gln Leu Lys Glu Lys Leu Glu Lys Ser Asp Val Arg
    145                 150                 155

CTT TAGTTTTTCC CCGTTTGAGA GCATTTCTGG ATATATTTTA CAACCACTCA ATAATGTA  660
Leu
160
```

( 2 ) INFORMATION FOR SEQ ID NO:12:

( i ) SEQUENCE CHARACTERISTICS:
( A ) LENGTH: 160 amino acids
( B ) TYPE: amino acid ( D ) TOPOLOGY: linear ( i i ) MOLECULE TYPE: protein ( x i ) SEQUENCE DESCRIPTION: SEQ ID NO:12:

| Met | Ala | Ala | Tyr | Ile | Ser | Ser | Lys | Glu | Arg | Lys | Ser | Met | Lys | Lys | Tyr |
| 1 | | | | 5 | | | | | 10 | | | | | 15 | |
| Ser | Leu | Val | Thr | Leu | Leu | Ser | Leu | Phe | Cys | Ile | Ser | His | Ala | Lys | Ala |
| | | | 20 | | | | | 25 | | | | | 30 | | |
| Gln | Thr | Ala | Thr | Leu | Thr | Asp | Glu | Tyr | Tyr | Lys | Lys | Ala | Leu | Glu | Asn |
| | | 35 | | | | | 40 | | | | | 45 | | | |
| Thr | Gln | Lys | Leu | Asp | Val | Ala | Lys | Ser | Gln | Thr | Ala | Glu | Ser | Ile | Tyr |
| | 50 | | | | | 55 | | | | | 60 | | | | |
| Glu | Ser | Ala | Thr | Gln | Thr | Ala | Asn | Lys | Ile | Lys | Asp | Ile | Asn | Asn | Gln |
| 65 | | | | | 70 | | | | | 75 | | | | | 80 |
| Leu | Ala | Asn | Leu | Lys | Ala | Asp | Thr | Lys | Thr | Lys | Pro | Glu | Gln | Leu | Gln |
| | | | | 85 | | | | | 90 | | | | | 95 | |
| Ala | Leu | Gln | Ile | Glu | Leu | Thr | Leu | Leu | Gln | Ala | Gln | Leu | Gln | Ala | Asp |
| | | | 100 | | | | | 105 | | | | | 110 | | |
| Thr | Leu | Lys | Ile | Gln | Ser | Leu | Ala | Met | Ile | Gln | Ala | Lys | Asp | Thr | Lys |
| | | 115 | | | | | 120 | | | | | 125 | | | |
| Thr | Lys | Glu | Glu | Leu | Arg | Glu | Glu | Gln | Thr | Gln | Lys | Lys | His | Glu | Asp |
| | 130 | | | | | 135 | | | | | 140 | | | | |
| Leu | Gln | Lys | Gln | Leu | Lys | Glu | Lys | Leu | Glu | Lys | Ser | Asp | Val | Arg | Leu |
| 145 | | | | | 150 | | | | | 155 | | | | | 160 |

( 2 ) INFORMATION FOR SEQ ID NO:13:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

AAAAGCTTGA AAAAATATAG CTTAGTCAC       29

( 2 ) INFORMATION FOR SEQ ID NO:14:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

AAGGATCCAG AAATGCTCTC AAAC       24